United States Patent
Kuroda et al.

(10) Patent No.: US 12,117,440 B2
(45) Date of Patent: Oct. 15, 2024

(54) METHOD FOR ISOLATING EXOSOME AND EXOSOME ISOLATION KIT

(71) Applicant: Hiroshima University, Higashi-Hiroshima (JP)

(72) Inventors: Akio Kuroda, Higashi-Hiroshima (JP); Takenori Ishida, Higashi-Hiroshima (JP)

(73) Assignee: Hiroshima University, Higashi-Hiroshima (JP)

( * ) Notice: Subject to any disclaimer, the term of this patent is extended or adjusted under 35 U.S.C. 154(b) by 1044 days.

(21) Appl. No.: 16/640,753

(22) PCT Filed: Jul. 25, 2018

(86) PCT No.: PCT/JP2018/027945
§ 371 (c)(1),
(2) Date: Jun. 8, 2021

(87) PCT Pub. No.: WO2019/039179
PCT Pub. Date: Feb. 28, 2019

(65) Prior Publication Data
US 2021/0389314 A1 Dec. 16, 2021

(30) Foreign Application Priority Data
Aug. 22, 2017 (JP) ................. 2017-159645

(51) Int. Cl.
*G01N 33/543* (2006.01)
*C07K 7/06* (2006.01)

(52) U.S. Cl.
CPC ......... *G01N 33/54326* (2013.01); *C07K 7/06* (2013.01)

(58) Field of Classification Search
CPC ............................ G01N 33/54326; C07K 7/06
See application file for complete search history.

(56) References Cited

FOREIGN PATENT DOCUMENTS

| EP | 3246703 | 11/2017 |
|---|---|---|
| JP | 2017038566 A | 2/2017 |
| JP | 2017044674 A | 3/2017 |
| WO | 2014168230 A1 | 10/2014 |
| WO | 2016/172598 A1 | 10/2016 |

OTHER PUBLICATIONS

Kosanović, Maja, and Miroslava Janković. "Isolation of urinary extracellular vesicles from Tamm-Horsfall protein-depleted urine and their application in the development of a lectin-exosome-binding assay." Bio Techniques vol. 57,3 143-9. Sep. 1, 2014, doi:10.2144/000114208 (Year: 2014).*
International Search Report for PCT/JP2018/027945 dated Oct. 23, 2018.
English Translation of International Preliminary Report on Patentability for PCT/JP2018/027945 dated Feb. 25, 2020.
Master Lesson of Exosome Handling, Edited by Takahiro Ochiya (2014), Yodosha Co., Ltd.
Ghosh A. et al., "Rapid Isolation of Extracellular . . . " PLOS One, Oct. 17, 2014, vol. 9, No. 10, pp. 1-12.
Office Action for JP 2019-538014 dated Mar. 17, 2020.
Wataru Nakai et al: "A novel affinity-based method for the isolation of highly purified extracellular vesicles", Scientific Reports, vol. 6, No. 1, Sep. 23, 2016.
Yang Hengwen et al: "A lysine-rich motif in the phosphatidylserine receptor PSR-1 mediates recognition and removal of apoptotic cells", Nature Communications, vol. 6, No. 1, Jan. 7, 2015.
Flynn Aaron D. et al: "Lipid-Targeting Peptide Probes for Extracellular Vesicles: Lipid-Targeting Peptide Probes", Journal of Cellular Physiology, vol. 231, No. 11, Nov. 1, 2016, pp. 2327-2332.
Ishida Takenori et al: "Application of peptides with an affinity for phospholipid membranes during the automated purification of extracellular vesicles", Scientific Reports, vol. 10, No. 1, Oct. 30, 2020.
Extended European Search Report for EP 18848051.1, dated Apr. 1, 2021.

* cited by examiner

*Primary Examiner* — Elizabeth C. Kemmerer
*Assistant Examiner* — McKenzie A Dunn
(74) *Attorney, Agent, or Firm* — Casimir Jones, S.C.; Robert A. Goetz

(57) ABSTRACT

The present invention provides a method for simply isolating exosomes from a sample containing exosomes. The present invention includes a complex forming step of forming a complex by binding an exosome in a sample to a particular peptide that contains lysines and is supported on a carrier and a dissociating step of dissociating the exosome from the complex by bringing the complex into contact with a dissociation buffer containing metal cations.

5 Claims, 9 Drawing Sheets

Specification includes a Sequence Listing.

METHOD FOR ISOLATING EXOSOME AND EXOSOME ISOLATION KIT

CROSS REFERENCE TO RELATED APPLICATIONS

This application is a U.S. National Stage application of PCT/JP2018/027945 filed on Jul. 25, 2018, which claims priority to Japanese patent application 2017-159645 filed on Aug. 22, 2017, the contents of both of which are incorporated herein by reference.

TECHNICAL FIELD

The present invention relates to a method for isolating an exosome and an exosome isolation kit.

BACKGROUND ART

An exosome is a particle covered with a membrane. The exosome is secreted from a cell and has a diameter of 20 nm through 120 nm. It is known that exosomes are present in a wide variety of biological fluids such as blood, saliva, urine, and cerebrospinal fluid, and each of the exosomes contains therein various substances such as a protein, mRNA, and microRNA (hereinafter, referred to as "miRNA"). Recently, it has been suggested that the exosome has an intercellular information exchange facility achieved via the substances contained in the exosome. Therefore, the exosomes are receiving attention as biomarkers for various diseases and vital phenomena.

Among the substances contained in the exosome, in particular, attention is being given to miRNA as a biomarker for a disease. miRNA is contained in an exosome, and therefore stably exists for a long time even in blood. Before now, more than 700 types of miRNA have been confirmed, and it is possible to accurately specify, for example, a tumor-generated organ by analyzing an expression pattern of a relatively smaller number of those miRNA. As such, a technique to isolate an exosome, which contains miRNA having information that is extremely important in a living body, is very important in the fields of medical treatment and the like.

Some methods have been reported so far as techniques to isolate or collect exosomes. Examples of such methods include (1) an ultra-centrifugal method, (2) pelleting down by centrifugation, (3) fractionation according to particle sizes, (4) immunoprecipitation, and the like (Non-patent Literature 1).

(1) The ultra-centrifugal method includes: a technique to isolate exosomes by precipitation by ultracentrifuging a sample (specifically, by carrying out centrifugation at 100000×g for 70 minutes two to three times) (sedimentation velocity fractionation); and a technique of strict fractionation carried out based on a size or density with use of a density gradient solution of cane sugar or the like (density gradient fractionation). In particular, the former is a standard method that is most generally employed.

(2) The pelleting down by centrifugation is a technique of concentration carried out by adding a reagent (polymer) to a sample and thus precipitating exosomes with use of a centrifuge.

(3) The fractionation according to particle sizes is a technique to capture exosomes by causing a sample to pass through a plurality of (typically, two to three) filters and can be advantageously carried out easily. For example, in a case where two filters are used, larger particles are removed with use of a top filter (first filter) having a pore size of approximately 200 nm, and then exosomes can be captured with use of a bottom filter (second filter) having a pore size of approximately 20 nm.

(4) The immunoprecipitation is a technique to collect exosomes having a surface in which a particular protein exists with use of magnetic beads on which an antibody against the protein is immobilized. In the immunoprecipitation, it is possible to capture an exosome having a surface in which a particular exosome antigen (for example, CD9, CD63, CD81, or the like) exists. Moreover, by changing an antibody to be used, it is possible to advantageously carry out immunoprecipitation targeting various antigens in a surface of exosome membrane.

CITATION LIST

Non-Patent Literature

Non-Patent Literature 1

"Master Lesson of Exosome Handling" edited by Takahiro OCHIYA (2014), YODOSHA CO., LTD.

SUMMARY OF INVENTION

Technical Problem

However, the above described conventional techniques to isolate or collect exosomes have the following problems.

(1) According to the ultra-centrifugal method, an ultra-centrifuge that is used in the method is expensive, and a centrifugation process takes a long time. Moreover, the ultra-centrifugal method is unsuitable for processing a large number of samples, and further proteins such as albumin, IgG, and proteosome may disadvantageously intrude in a purified product when a serum sample is used.

(2) The pelleting down by centrifugation is merely a concentration method, and therefore notably many contaminating proteins may intrude depending on a sample used. Moreover, it is necessary to optimize a composition of a reagent for each of samples such as culture supernatant, serum, and urine, and thus the process is complicated.

(3) In the fractionation according to particle sizes, a filter may clog up when a sample contains many impurities. Moreover, it is necessary to dissolve exosomes, and thus the fractionation according to particle sizes has a problem that only a nucleic acid is to be analyzed.

(4) The immunoprecipitation is a method targeting a certain antigen molecule. Therefore, although it is possible to capture an exosome in which the antigen molecule is expressed, an exosome in which the antigen molecule is not expressed cannot be captured. That is, the method has a problem that only some of exosomes in a sample can be captured. Furthermore, in a complex of a collected exosome and an antibody, the exosome and the antibody are firmly bound together. Therefore, in order to isolate an intact exosome by dissociating the exosome from the antibody, it is necessary to carry out the dissociation under strict conditions involving denaturation of a protein. As such, it is difficult to isolate an exosome in an intact state.

Under the circumstances, a novel exosome isolation technique is demanded which can overcome the above problems. An object of the present invention is to provide a method and a kit for simply isolating an exosome in an intact state (or in a substantially intact state).

Solution to Problem

As a result of diligent study for attaining the object, the inventors of the present invention have found that it is possible to simply isolate an exosome in an intact state (or in a substantially intact state) by using a particular peptide and a particular dissociation buffer, and thus the inventors have accomplished the present invention.

That is, an embodiment of the present invention is configured as follows:

A method for isolating an exosome from a sample containing the exosome, the method including: a complex forming step of forming a complex by binding the exosome to a peptide supported by a carrier, the peptide containing four or more lysines which are close to each other, the carrier being capable of supporting the peptide and, in binding the exosome to the peptide, (i) the sample, the peptide, and the carrier being brought into contact with each other or (ii) the sample and the peptide supported by the carrier being brought into contact with each other; and a dissociating step of dissociating the exosome from the complex by bringing the complex which has been obtained in the complex forming step into contact with a dissociation buffer containing metal cations.

Advantageous Effects of Invention

An embodiment of the present invention can bring about an effect of simply isolating an exosome in an intact state (or in a substantially intact state).

DESCRIPTION OF EMBODIMENTS

Figure 1:
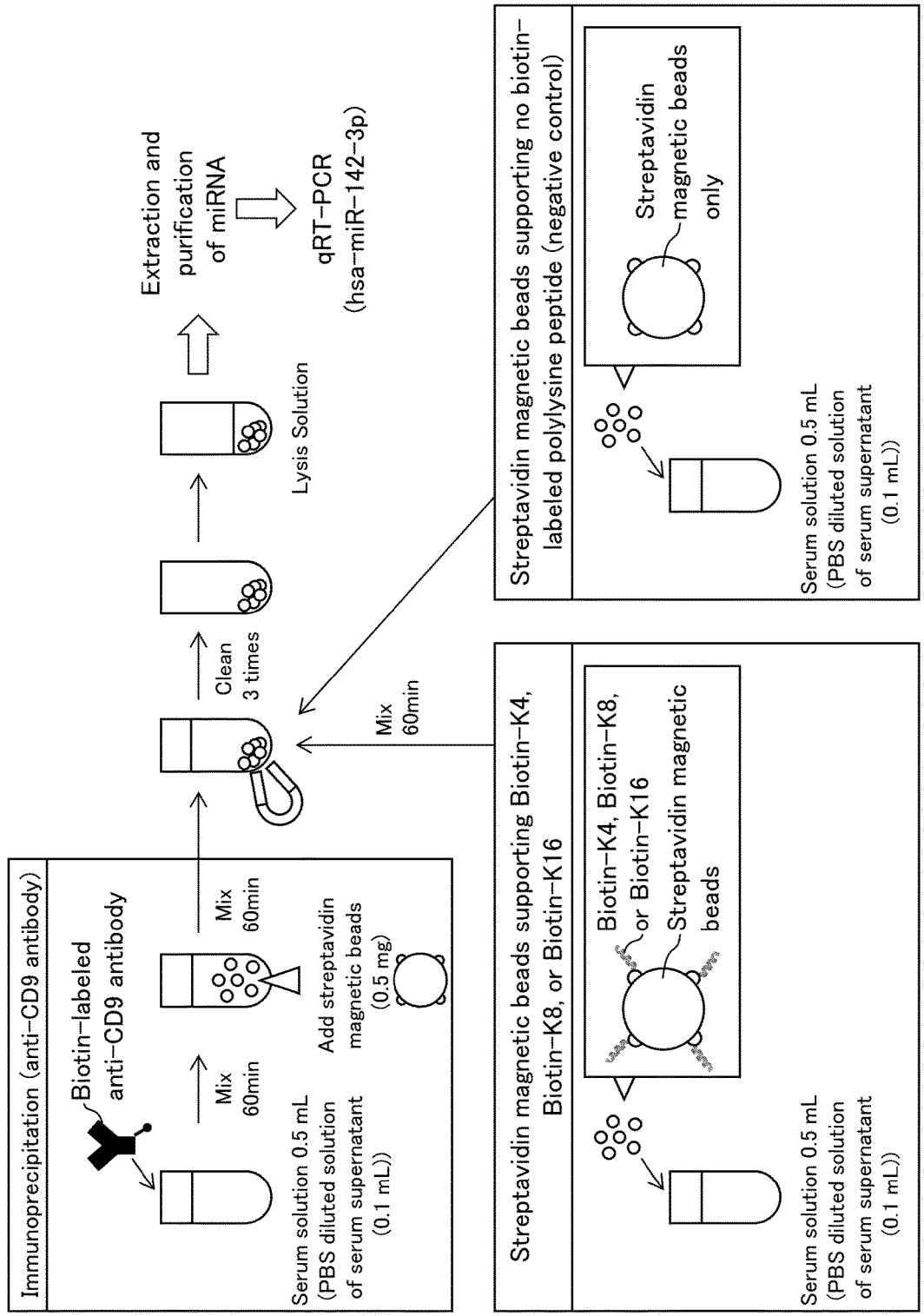
FIG. 1 is a view schematically illustrating experimental procedures in Test Example 1.

The following description will discuss an embodiment of the present invention. The present invention is, however, not limited to the embodiment below. The present invention is not limited to arrangements described below, but may be altered in various ways by a skilled person within the scope of the claims. The present invention also encompasses, in its technical scope, any embodiment or working example derived by combining technical means disclosed in differing embodiments or working examples. Note that all scientific literatures and patent literatures described in this specification are incorporated herein as reference literatures. Numerical ranges such as "A to B" herein mean "not less than A (i.e., the range includes A and numerals greater than A) and not more than B (i.e., the range includes B and numerals smaller than B)" unless otherwise stated.

In this specification, the term "peptide" is used interchangeably with the term "polypeptide" and means a compound in which two or more amino acids bind together by a peptide bond. In this specification, amino acids are represented with use of one-letter notation or three-letter notation as appropriate in accordance with the rules provided for in IUPAC and IUB.

[1. Exosome Isolation Method]

A method for isolating an exosome in accordance with an embodiment of the present invention (hereinafter referred to as "isolation method of the present invention" as appropriate) is a method for isolating an exosome from a sample containing the exosome, the method including: a complex forming step of forming a complex by binding the exosome to a peptide supported by a carrier, the peptide containing four or more lysines which are close to each other, the carrier being capable of supporting the peptide and, in binding the exosome to the peptide, (i) the sample, the peptide, and the carrier being brought into contact with each other or (ii) the sample and the peptide supported by the carrier being brought into contact with each other; and a dissociating step of dissociating the exosome from the complex by bringing the complex which has been obtained in the complex forming step into contact with a dissociation buffer containing metal cations.

The method for isolating an exosome in accordance with an embodiment of the present invention having the above features brings about the following effects (1) through (3):

(1) It is not necessary to use an ultracentrifuge or the like, and it is therefore possible to simply isolate exosomes in a short time.

(2) The bind of lysines to the exosome membrane is utilized, and it is therefore possible to widely capture and isolate exosomes regardless of expression states of antigen molecules in the exosomes.

(3) An exosome is dissociated from a complex under a mild (gentle) condition with use of a dissociation buffer containing metal cations which hardly influences a membrane structure of the exosome and a structure of a protein that exists in the membrane. It is therefore possible to isolate the exosome without damaging the exosome (in other words, in an intact state or in a substantially intact state).

By isolating an exosome in an intact state (or a substantially intact state), it is possible to use the exosome, for example, (1) in functional analysis of a physiological effect or the like of the exosome or (2) as a biomarker (a protein derived from the exosome, a nucleic acid such as miRNA).

Exosomes are expected to be applied to treatment of a wide variety of diseases such as cancers, Alzheimer's disease, myocardial infarction, cerebral infarction, and infectious diseases. In view of this, by isolating an exosome in an intact state (or a substantially intact state), the isolated exosome itself can be used as (3) a therapeutic agent or (4) a carrier in a drug delivery system. In particular, in a case where the exosome is used as a therapeutic agent ((3)

above), the exosome can be (A) used subsidiarily in regenerative medical techniques, (B) used for the purpose of immunoregulation, and (C) used as a vaccine (Reference Literature: Experimental Medicine (*Jikken Igaku*), 2016, vol. 34, p 1390-1396: Next-generation medical care created by exosomes).

The above (A) through (C) will be explained with reference to specific examples. Exosomes derived from mesenchymal stem/stromal cells (MSC) are exosomes which have been mostly researched. The MSC-derived exosomes are known to have a function to facilitate cell division, an anti-apoptotic function, and an anti-inflammatory function. This makes it possible to inhibit secondary damage on tissues around a damaged tissue, and to facilitate recovery of the damaged tissue. Therefore, the MSC-derived exosomes are expected to be applied to regeneration of skins and livers, and to recovery from many diseases such as myocardial infarction ((A) subsidiary use in regenerative medical techniques). Moreover, the MSC-derived exosome has multiplex immunoregulation functions and is expected to be applied to treatment of autoimmune disease and to immunoregulation after organ transplantation ((B) use for the purpose of immunoregulation).

An exosome, which is secreted from an antigen presenting cell and is collected after causing a cancer antigen peptide to react with the antigen presenting cell, presents an antigen peptide and has a function to activate $CD4^+$ and $CD8^+$ T cells. The cancer cell-derived exosome may be used as a vaccine by directly using the exosome as an antigen ((C) use as vaccine).

The following description will first discuss materials which are used in the method for isolating an exosome in accordance with an embodiment of the present invention, and then discuss steps in the method for isolating an exosome.

[1-1. Materials]
(Sample)

According to the isolation method of the present invention, a "sample containing exosomes" (herein, sometimes simply referred to as "sample") is not particularly limited in terms of configuration, provided that the sample is a mixture containing exosomes. The sample can be, for example, a biological sample containing exosomes.

In this specification, the "biological sample" means a specimen taken from inside a body of an organism. Examples of the biological sample include, but not limited to, blood, blood plasma, serum, saliva, urine, lacrimal fluid, sweat, breast milk, amniotic fluid, cerebrospinal fluid (spinal fluid), bone marrow fluid, pleural effusion, ascites, synovial fluid, aqueous humor, vitreous humor, and the like. Selection of the biological sample can be carried out as appropriate by a person skilled in the art in accordance with a purpose. For example, from the viewpoint of easiness in collection, blood, blood plasma, serum, saliva, urine, or the like is preferably used.

According to an embodiment of the present invention, a source of the biological sample is not particularly limited, provided that the biological sample is derived from species having exosomes. A species from which the biological sample is to be derived is preferably, for example, a mammal. Examples of the mammal include a mouse (Mus musculus), a cattle (Bos Taurus), a human (Homo sapiens), and the like.

(Peptide)

A peptide which is used in the isolation method of the present invention (hereinafter, referred to as "peptide of the present invention" as appropriate) is a peptide containing four or more lysines which are close to each other, and the peptide can be bound to an exosome in the sample.

In the descriptions of the peptide of the present invention, the phrase "close to each other" means that the lysines constituting the peptide of the present invention are adjacent to each other (in other words, the lysines are consecutive) or 1 to 5 (more preferably 1 to 3, further preferably 1) amino acids which are not lysine exist between the lysines.

The peptide of the present invention contains the four or more lysines which are close to each other, and therefore the peptide of the present invention can bind to the exosome. The present invention is not restricted to a particular theory. Here, lysines have positive electric charges, and the exosome membrane is negatively charged as with a cell membrane. This is because the inventors deem that the peptide of the present invention containing four or more lysines which are close to each other can bind to the exosome.

As long as the peptide of the present invention contains four or more lysines which are close to each other, the peptide can bind to an exosome with binding strength with which the exosome can be isolated. Note that the peptide of the present invention contains preferably five or more lysines which are close to each other, more preferably six or more lysines which are close to each other, further preferably seven or more lysines which are close to each other, particularly preferably eight or more lysines which are close to each other. In a case where the peptide of the present invention has the above feature, the peptide advantageously more easily binds to an exosome.

The peptide of the present invention is not particularly limited in other features, provided that the peptide contains four or more lysines which are close to each other, and can be a peptide constituted by only lysines, or can be a peptide containing an amino acid in addition to the lysines. The peptide of the present invention can be a composite peptide which further includes a structure such as a sugar chain or an isoprenoid group in addition to a peptide. Amino acids which are contained in the peptide of the present invention can be modified. The amino acids contained in the peptide of the present invention can be L-type amino acids or can be D-type amino acids.

The peptide of the present invention can be easily prepared in accordance with a publicly known arbitrary method in this field. For example, the peptide of the present invention can be expressed by a transformant into which a peptide expression vector is introduced or can be chemically synthesized. That is, a polynucleotide that encodes the peptide of the present invention is also encompassed in the scope of the present invention. The chemosynthetic method can be a solid phase method or a liquid phase method. In the solid phase method, for example, any of commercially available peptide synthesis devices (Model MultiPep RS (Intavis AG) or the like) can be used. Alternatively, commercially available polylysine can be used as the peptide of the present invention. The commercially available polylysine is not particularly limited and can be poly-L-lysine (molecular weight: 4,000-15,000; available from Sigma-Aldrich), a poly-L-lysine solution (molecular weight: 150,000-300,000; available from Sigma-Aldrich), and the like which were used in Examples described later.

The peptide of the present invention can be constituted by at least four lysines, and therefore a lower limit of the molecular weight of the peptide of the present invention is $530.7[=(146.19\times4)-(18.02\times3)]$. An upper limit of the molecular weight of the peptide of the present invention is not particularly limited and can be approximately 300,000 from the viewpoint of operationality such as solubility and viscosity.

The peptide of the present invention can be constituted by a peptide having a single molecular weight or can be constituted by a mixture of peptides having different molecular weights.

(Carrier)

A carrier used in the isolation method of the present invention (hereinafter referred to as "carrier of the present invention" as appropriate) means a carrier which can support the peptide of the present invention. The carrier of the present invention binds to the peptide of the present invention which binds to an exosome, and can thus form a complex in which the exosome, the peptide of the present invention, and the carrier of the present invention bind together in this order.

According to the isolation method of the present invention, a complex containing an exosome can be efficiently and simply isolated with use of the carrier.

The carrier is not particularly limited in features, provided that the carrier is a structure which can directly or indirectly support (hold) the peptide of the present invention. The carrier of the present invention is preferably a support that does not deteriorate the function of the peptide of the present invention which binds to the carrier. Examples of the carrier of the present invention include glass, a nylon membrane, a semiconductor wafer, latex particles, cellulose particles, microbeads, silica beads, magnetic beads, and the like. The carrier of the present invention is particularly preferably magnetic beads because magnetic beads make it possible to easily collect complexes containing exosomes and isolate the exosomes. Magnetic beads are widely used in separating and refining proteins, DNA, cells, and the like, and are a carrier which a person skilled in the art can sufficiently understand.

(Method for Binding Peptide of the Present Invention to Carrier of the Present Invention)

As above described, the carrier of the present invention can support the peptide of the present invention by binding the peptide of the present invention to the carrier of the present invention.

According to an embodiment of the present invention, a method for binding the peptide to the carrier is not particularly limited, and it is possible to employ a known method as appropriate. The peptide can bind to the carrier directly or indirectly. For example, it is possible to form an indirect bond of the peptide and the carrier via a bond of biotin and streptavidin with use of the peptide of the present invention binding to biotin and the carrier of the present invention binding to streptavidin. Streptavidin constitutes a tetramer, and therefore four "biotins binding to peptides" can bind to one "streptavidin binding to a carrier". That is, in a case where the carrier of the present invention has one streptavidin, four peptides of the present invention bind to the one carrier of the present invention. Therefore, the carrier of the present invention can bind to one or more exosomes via the four peptides of the present invention. From this, binding force between the carrier of the present invention and the exosome becomes extremely high, or the carrier of the present invention can bind to a plurality of exosomes. From this, with use of the binding method described above, it is possible to isolate exosomes at an extremely high yield.

The method of binding biotin to the peptide, in other words, the method for preparing a peptide (in this specification, also referred to as "biotin-labeled peptide" as appropriate) to which biotin has bound is not limited to a particular one. For example, biotin can be directly bound to the peptide or can be indirectly bound to the peptide. From the viewpoint of maintaining a structure of the peptide and a function based on the structure as normally as possible, it is preferable that biotin is indirectly bound to the peptide. In a case where biotin is bound indirectly to the peptide, for example, an arbitrary linker is linked with the peptide of the present invention, and then biotin is bound to the linker which is linked with the peptide. From the viewpoint of maintaining a structure of the peptide and a function based on the structure as normally as possible, it is preferable that the peptide has a linker(s) for binding to biotin at an amino terminus (N-terminus) and/or a carboxy terminus (C-terminus) thereof.

The linker can be a linker constituted by polypeptide (in this specification, also referred to as "peptide linker") or can be a known crosslinking agent or spacer arm that can link biotin with a peptide.

In a case of the peptide linker, a length of the linker and a type of amino acids constituting the linker can be set by a person skilled in the art as appropriate. The length of the peptide linker is not particularly limited, and a linker constituted by typically 1 to 20, preferably 1 to 10 (for example, 10, 9, 8, 7, 6, 5, 4, 3, 2, 1) amino acids is employed. The type of amino acid used in the peptide linker is also not particularly limited and, for example, glycine (G), serine (S), threonine (T), and/or the like can be used. In particular, a peptide linker containing GGS, GGGS (SEQ ID NO: 1), GGGGS (SEQ ID NO: 2), or the like, or a peptide linker containing repetitions of those sequences (for example, GGGSGGGS (SEQ ID NO: 3), GGGSGGGSGGGS (SEQ ID NO: 4), or the like) is preferably used.

Examples of the known crosslinking agent that can link biotin with the peptide include, but not limited to, N-succinimidyl amide, N-maleinimide, isothiocyanate, bromoacetamide, and the like.

The spacer arm is not particularly limited provided that the spacer arm is a known spacer arm. For example, a spacer arm containing a carbon chain is used or, more preferably, hexanonate having a carbon chain of 6 carbon atoms is used.

The method for preparing streptavidin binding to the carrier is not limited to a particular one. For example, streptavidin can be directly bound to the carrier or can be indirectly bound to the carrier. It is possible to prepare streptavidin binding to the carrier in accordance with a publicly known method as appropriate. Note that the magnetic beads to which streptavidin has been bound are commercially available and are known as, for example, Dynabeads (Registered Trademark, Thermo Fisher Scientific K.K.) or the like.

It is possible to bind one type of peptide to the carrier or it is possible to bind a combination of two or more types of peptides to the carrier. In a case where the combination of two or more types of peptides is used, the combination is not limited in particular.

(Dissociation Buffer)

According to the isolation method of the present invention, in a dissociating step (described later), an exosome is dissociated from the complex by bringing the complex into contact with a dissociation buffer (hereinafter, referred to as "dissociation buffer of the present invention" as appropriate) containing metal cations, and thus the exosome is isolated. The dissociation buffer of the present invention does not contain a surfactant, a protein denaturant, and/or the like and makes it possible to dissociate an exosome from the complex under a mild (gentle) condition. Therefore, it is possible to isolate the exosome in an intact state (or in a substantially intact state). The inventors of the present invention found for the first time that such a mild dissociation buffer can dissociate a bond between the peptide of the present invention and an exosome, and a person skilled in the art who does not know this novel idea cannot easily arrive at the present invention. Moreover, the effect of simply isolating an exosome in an intact state (or in a substantially intact state) is a remarkable and advantageous effect of the present invention.

Examples of the metal cations contained in the dissociation buffer of the present invention include, but not limited to, monovalent metal cations such as sodium ions, potassium ions, lithium ions, silver ions, and copper (I) ions; bivalent metal cations such as magnesium ions, calcium ions, zinc ions, nickel ions, barium ions, copper (II) ions, iron (II) ions, tin (II) ions, cobalt (II) ions, and lead (II) ions; trivalent metal cations such as aluminum ions and iron (III) ions; and the like. Among those metal cations, sodium ions, potassium ions, magnesium ions, zinc ions, and nickel ions are preferable as the metal cations contained in the dissociation buffer of the present invention because those metal cations are highly water-soluble. The dissociation buffer of the present invention preferably contains solely or in combination sodium ions, potassium ions, and magnesium ions from among the above metal cations so as to sufficiently dissociate an exosome from the complex.

An object of the present invention is to simply isolate an exosome in an intact state (or in a substantially intact state). Therefore, "isolating an exosome in an intact state (or in a substantially intact state)" in the isolation method of the present invention means to separate substances (for example, protein and the like) other than an exosome in the sample and thus isolate the exosome in the sample without damaging (or substantially without damaging) the exosome. In other words, "isolating an exosome in an intact state (or in a substantially intact state)" in the isolation method of the present invention means to separate substances other than the exosome in the sample and thus isolate the exosome in the sample in a state in which a membrane structure (specifically, lipid bilayer membrane structure) of the exosome is maintained (or is substantially maintained) and in a state in which a structure of a protein existing in the membrane is maintained (or is substantially maintained).

The dissociation buffer can contain a substance in addition to the metal cations to an extent that the substance does not influence the membrane structure of the exosome and the structure of the protein existing in the membrane.

A concentration of the metal cations in the dissociation buffer is not limited to a particular one, provided that it is possible to dissociate an exosome from the complex and a membrane structure of the exosome and a structure of a protein existing in the membrane are not influenced. That is, an optimal concentration of cations can vary in accordance with binding strength between the peptide of the present invention used and an exosome, a type (valence) of metal cations, and the like. Therefore, the optimal concentration can be determined based on study as appropriate. The concentration of metal cations in the dissociation buffer of the present invention is not particularly limited and is, for example, preferably 0.01 M to 5 M, more preferably 0.05 M to 2 M, further preferably 0.1 M to 1 M, particularly preferably 0.3 M to 0.7 M.

pH of the dissociation buffer can be set as appropriate. pH of the dissociation buffer is preferably 5 to 10, more preferably 6 to 9, further preferably 7 to 8, particularly preferably 7.3 to 7.5. The dissociation buffer preferably has pH falling within the above ranges because a membrane structure of an exosome and a structure of a protein existing in the membrane are not influenced when the pH falls within the above ranges.

[1-2. Processes]

(Complex Forming Step)

A complex forming step included in the isolation method of the present invention (hereinafter, referred to as "complex forming step of the present invention" as appropriate) is a complex forming step of forming a complex (in which an exosome, the peptide of the present invention, and the carrier of the present invention are bound together in this order; hereinafter referred to as "complex of the present invention" as appropriate) by binding the exosome to the peptide of the present invention supported by the carrier of the present invention, in binding the exosome to the peptide, (i) the sample containing exosomes, the peptide, and the carrier being brought into contact with each other or (ii) the sample and the peptide supported by the carrier being brought into contact with each other. That is, in the complex forming step of the present invention, (i) it is possible to form a complex in which the exosome, the peptide of the present invention, and the carrier of the present invention are bound together in this order after the peptide, the carrier, and the sample are brought into contact with each other in a state in which the peptide is not supported by the carrier or (ii) the complex of the present invention can be formed by bringing the peptide and the sample into contact with each other in a state in which the peptide has already been supported by the carrier. Note that the latter aspect is more preferable from the viewpoint of more efficiently forming the complex of the present invention.

The method of bringing the sample containing exosomes, the peptide of the present invention, and the carrier of the present invention into contact with each other is not particularly limited, provided that the method is carried out under conditions in which the exosome in the sample, the peptide, and the carrier are bound to each other and thus the complex of the present invention can be formed. For example, a method can be employed in which the peptide of the present invention and the carrier of the present invention are added to the sample, and the peptide, the carrier, and the sample are mixed. An order of adding and mixing in bringing the sample, the peptide of the present invention, and the carrier of the present invention into contact with each other is not limited to a particular one. For example, (1) it is possible to simultaneously add the peptide of the present invention and the carrier of the present invention to the sample and then mix them, (2) the peptide of the present invention can be added to and mixed with the sample first and then the carrier of the present invention can be added and mixed, and (3) the carrier of the present invention can be added to and mixed with the sample first and then the peptide of the present invention can be added and mixed. Note, however, that the above procedure (2) may be preferable because the peptide of the present invention binds to the exosome first and then the peptide of the present invention binds to the carrier of the present invention in the above procedure (2). By bringing the sample, the peptide, and the carrier into contact with each other with the above described method, the complex of the present invention containing the exosome, the peptide, and the carrier can be formed.

The method of bringing the sample and the peptide of the present invention supported by the carrier of the present invention into contact with each other is not particularly limited, provided that the method is carried out under conditions in which the exosome in the sample and the peptide supported by the carrier are bound to each other and thus the complex of the present invention can be formed. For example, a method can be employed in which the peptide of the present invention supported by the carrier of the present invention is added to and mixed with the sample.

A time for which the sample, the peptide of the present invention, and the carrier of the present invention make contact with each other or a time for which the sample and the peptide of the present invention supported by the carrier of the present invention make contact with each other is not limited, provided that the time is sufficient for forming the complex of the present invention. The time can be determined as appropriate based on study of an optimal condition.

In bringing the sample containing exosomes, the peptide of the present invention, and the carrier of the present invention into contact with each other, it is possible to use a column containing a carrier (in this specification, referred to as "carrier column") which has been prepared by filling, for example, a columnar or cylindrical container (column) with the carrier of the present invention. The method of obtaining the complex of the present invention by causing a solution containing the sample and a solution containing the peptide to permeate the carrier column is not particularly limited, provided that the method is carried out under conditions in which the exosome in the sample, the peptide of the present invention, and the carrier of the present invention are bound to each other and thus the complex of the present invention can be formed. For example, the following methods (1) through (3) can be employed: (1) A solution containing the peptide of the present invention is added to the carrier column so as to permeate the carrier column so that the carrier of the present invention is bound to the peptide of the present invention, and then a solution containing the sample is added to the carrier column so as to permeate the carrier column, and thus the complex of the present invention is formed; (2) The sample and the peptide of the present invention are brought into contact with each other in advance by adding and mixing the peptide of the present invention with the sample and thus a complex (exosome-peptide complex) is formed in which the exosome in the sample is bound to the peptide, and then a solution containing the exosome-peptide complex is added to the carrier column so as to permeate the carrier column, and thus the peptide of the present invention and the carrier of the present invention are bound to each other to form the complex of the present invention; (3) A solution containing the sample and a solution containing the peptide of the present invention are simultaneously added to the carrier column so as to permeate the carrier column, and thus the complex of the present invention is formed.

In the above methods (1) through (3), a time for which the carrier column makes contact with the peptide and/or the sample or the sample containing the exosome-peptide complex is preferably a time sufficient for forming the complex of the present invention from the exosome in the sample, the peptide, and the carrier. The time can be set as appropriate by adjusting a permeation rate of the sample solution (i.e., a solution containing the sample containing exosomes and/or the peptide of the present invention, or a solution containing the exosome-peptide complex) into the carrier column or adjusting a time period from when the sample solution is added to when the permeation is started, or the like.

In bringing the sample containing exosomes into contact with the peptide of the present invention supported by the carrier of the present invention, it is possible to use a column (in this specification, referred to as "peptide column") which has been prepared by filling, for example, a columnar or cylindrical container (column) with the carrier of the present invention supporting the peptide of the present invention. By causing the solution containing the sample to permeate the peptide column, it is possible to bring the sample into contact with the peptide of the present invention supported by the carrier of the present invention, and thus the complex of the present invention can be obtained. A time for which the peptide column and the sample make contact with each other is preferably a time sufficient for forming the complex of the present invention from the exosome in the sample and the peptide of the present invention supported by the carrier of the present invention. The time can be set as appropriate by adjusting a permeation rate of the solution containing the sample or adjusting a time period from when the solution is added to when the permeation is started, or the like.

A physical method for causing the sample solution to permeate the carrier column or the peptide column can be a conventionally known method. For example, the following methods (1) through (3) can be employed:

(1) The sample solution is added to the top of the carrier column (or peptide column) placed in the vertical direction, and the sample solution is caused to permeate the carrier column (or peptide column) by the gravity.

(2) The sample solution is added to one side of the carrier column (or peptide column), and the sample solution is pressurized on the side on which the sample solution has been added or the sample solution is sucked from a side opposite to the side on which the sample solution has been added, and thus the sample solution is caused to permeate the carrier column (or peptide column).

(3) The sample solution is added on one side of the carrier column (or peptide column), then the carrier column (or peptide column) is put in a centrifugation tube, then the centrifugation tube is subjected to centrifugal separation, and thus the sample solution is caused to permeate the carrier column (or peptide column). Note that the above method (3) is a method using a so-called conventionally known spin column.

(Dissociating Step)

A dissociating step included in the isolation method of the present invention (hereinafter, referred to as "dissociating step of the present invention" as appropriate) is a step of dissociating the exosome from the complex of the present invention by bringing the complex which has been obtained in the complex forming step into contact with the dissociation buffer of the present invention containing metal cations.

The method of bringing the complex of the present invention into contact with the dissociation buffer of the present invention is not particularly limited, provided that the method is carried out under conditions in which an exosome is dissociated from the complex of the present invention. For example, a method can be employed in which the dissociation buffer of the present invention is added to a container containing the complex of the present invention, and then the dissociation buffer and the complex are mixed. A time for which the complex of the present invention makes contact with the dissociation buffer of the present invention is not particularly limited, provided that the time is sufficient for dissociating an exosome from the complex. By the contact between the complex of the present invention and the dissociation buffer of the present invention, the exosome is dissociated from the complex of the present invention and is transferred to the dissociation buffer. Then, by separating the carrier of the present invention from the dissociation buffer to isolate the dissociation buffer, the exosome can be isolated.

In the dissociating step of the present invention, the peptide of the present invention can keep binding to the carrier of the present invention or can be dissociated from the carrier of the present invention. Moreover, after the separation, the peptide of the present invention can be contained in the isolated dissociation buffer. From the viewpoint of isolating an exosome with higher purity, the peptide of the present invention preferably keeps binding to the carrier of the present invention in the dissociating step of the present invention, and it is preferable that the peptide of the present invention is not contained in the isolated dissociation buffer after the separation.

In a case where the column is used in the complex forming step, the complex of the present invention can be brought into contact with the dissociation buffer of the present invention by causing the dissociation buffer of the present invention to permeate the column in which the complex of the present invention has been formed in the complex forming step. A physical method of causing the dissociation buffer of the present invention to permeate the column can be the methods (1) through (3) described above in the section of (Complex forming step). In a case where the column has been brought into contact with the dissociation buffer of the present invention, an exosome is dissociated from the complex and is then transferred to the dissociation buffer. From this, the exosome can be isolated by isolating the dissociation buffer which has permeated the column.

The isolation method of the present invention can include other step(s) in addition to the complex forming step and the dissociating step which have been described above. Those other steps can be, for example, a cleaning step and a collecting step.

(Collecting Step)

The collecting step is carried out between the complex forming step and the dissociating step. The collecting step is a step of collecting the complex of the present invention obtained in the complex forming step. In the collecting step, a conventionally known method can be employed as appropriate in accordance with the complex forming step, the carrier, and the like.

In a case where the carrier is the structure as described in the section (Carrier) in [1-1. Materials] above, it is possible to collect the carrier containing the complex of the present invention by centrifugal separation. For example, it is possible to collect the carrier containing the complex of the present invention by carrying out centrifugation under a condition of 500 g to 4000 g.

In a case where the carrier is magnetic beads, it is possible to easily collect the carrier by externally applying magnetic force with use of a magnetic substance such as a conventionally known magnetic stand. In a case where the carrier is magnetic beads and is collected with use of a magnetic substance, the following advantages (1) and (2) are achieved, as compared with a case where the centrifugation method is employed: (1) The carrier which is magnetic beads is attracted by the magnetic substance, and therefore supernatant can be substantially completely removed, and purity of obtained exosomes becomes higher; (2) In removing supernatant, magnetic beads are less likely to be removed together, and it is therefore possible to prevent a loss of obtained exosomes (i.e., it is possible to improve an exosome isolation ratio).

Note that, in a case where the carrier column or the peptide column is used in the complex forming step of the present invention, the carrier containing the complex of the present invention is left in the column. Therefore, the above collecting step is not needed.

(Cleaning Step)

The isolation method of the present invention preferably further includes a cleaning step that is carried out before the dissociating step.

The cleaning step is a step of cleaning the collected complex of the present invention or the complex of the present invention in the column with use of an appropriate cleaning liquid an appropriate number of times. The cleaning step is not particularly limited in type of used cleaning liquid and in number of times of cleaning, provided that the cleaning step is carried out under conditions in which the complex is not dissociated.

The cleaning liquid used in the cleaning step can be, for example, a physiological saline solution or a phosphate buffered saline (PBS).

In a case where an embodiment of the present invention includes the collecting step, the cleaning step can be a method as follows: (1) The carrier containing the collected complex of the present invention is mixed with the cleaning liquid, and thus the carrier is resuspended in the cleaning liquid. (2) The carrier containing the complex of the present invention is collected again (that is, the carrier containing the complex of the present invention is separated from the cleaning liquid).

In a case where the carrier column or the peptide column is used in the complex forming step of the present invention, an appropriate amount of the cleaning liquid can be caused to permeate the column in which the complex of the present invention has been formed.

[2. Exosome Isolation Kit]

An exosome isolation kit in accordance with an embodiment of the present invention (hereinafter, referred to as "kit of the present invention" as appropriate) is a kit for carrying out the isolation method of the present invention. The kit includes the peptide of the present invention, the carrier of the present invention, and the dissociation buffer of the present invention, which have been described above. Therefore, the descriptions of [1. Exosome isolation method] can be applied to the descriptions of the features of the kit.

The peptide of the present invention and the carrier of the present invention can be contained in the kit of the present invention in a state in which the peptide of the present invention is supported by the carrier of the present invention in advance or can be contained separately in the kit of the present invention.

The kit of the present invention can contain magnetic beads, magnetic beads on which streptavidin is immobilized, a magnetic substance such as a magnetic stand, biotin, and/or the like.

The kit of the present invention can include a container (for example, a bottle, a plate, a tube, a dish, a column, or the like) for containing a particular material, in addition to the above features. The kit of the present invention can include a container containing a diluent, a solvent, a cleaning liquid, or another reagent. The term "include (including)" used in the descriptions of the kit of the present invention can intend a state in which a subject is contained in any of containers constituting the kit.

The kit of the present invention can include an instruction manual for carrying out the isolation method of the present invention.

Aspects of the present invention can also be expressed as follows:

An embodiment of the present invention is configured as follows:

[1] A method for isolating an exosome from a sample containing the exosome, the method including: a complex forming step of forming a complex by binding the exosome to a peptide supported by a carrier, the peptide containing four or more lysines which are close to each other, the carrier being capable of supporting the peptide and, in binding the exosome to the peptide, (i) the sample, the peptide, and the carrier being brought into contact with each other or (ii) the sample and the peptide supported by the carrier being brought into contact with each other; and a dissociating step of dissociating the exosome from the complex by bringing the complex which has been obtained in the complex forming step into contact with a dissociation buffer containing metal cations.

[2] The method described in [1], in which the lysines contained in the peptide are consecutive.

[3] The method described in [1] or [2], in which the peptide contains eight or more lysines.

[4] The method described in any one of [1] through [3], in which the carrier is magnetic beads.

[5] An exosome isolation kit for carrying out the method described in any one of [1] through [4], the exosome isolation kit including the peptide, the carrier, and the dissociation buffer.

EXAMPLES

The following description will discuss an embodiment of the present invention in greater detail with reference to Examples. Note, however, that the present invention is not limited only to the Examples.

Experiment Method

<1> Preparation of Magnetic Beads Supporting Peptide (Polylysine-Immobilized Magnetic Beads)

A peptide contained four or more lysines which are close to each other was bound to (caused to be supported by) magnetic beads (carrier), and thus magnetic beads on which the peptide was supported were prepared.

As the carrier, magnetic beads on which streptavidin was immobilized (available from VERITAS; Dynabeads M-280 streptavidin) were used (in this specification, also referred to as "streptavidin magnetic beads").

As the peptide, a peptide contained (i) a linker peptide constituted by GGGSGGGS (SEQ ID NO: 3) or GGGSGGGSGGGS (SEQ ID NO: 4) and (ii) a sequence constituted by consecutive 4, 8, or 16 lysine residues was used (hereinafter, referred to as "polylysine peptide"). Amino acids used in Examples were all L-type amino acids. Further, in the polylysine peptide, the N-terminus of the polylysine peptide was bound to biotin for binding to magnetic beads (carrier) having streptavidin. The polylysine peptide to which biotin is bound is hereinafter referred to as "biotin-labeled polylysine peptide". The biotin-labeled polylysine peptides used in Examples were prepared by contract synthesis by Eurofins Genomics.

Names of three biotin-labeled polylysine peptides used in Examples and amino acid sequences of polylysine peptides included in the respective biotin-labeled polylysine peptides are as follows:

1. Biotin-K4; obtained by modifying, with biotin, the N-terminus of a peptide having an amino acid sequence of GGGSGGGSGGGSKKKK (SEQ ID NO: 5).
2. Biotin-K8; obtained by modifying, with biotin, the N-terminus of a peptide having an amino acid sequence of GGGSGGGSGGGSKKKKKKKK (SEQ ID NO: 6).
3. Biotin-K16; obtained by modifying, with biotin, the N-terminus of a peptide having an amino acid sequence of GGGSGGGSKKKKKKKKKKKKKKKK (SEQ ID NO: 7).

By utilizing interaction between biotin and streptavidin, specifically, with a method below, magnetic beads on which a peptide was supported were prepared.

(1) 50 µL (0.5 mg) of streptavidin magnetic beads were added to a 1.5 mL microtube (simply referred to as "tube"), then the tube was set on a magnet stand and left still for 1 minute, and then supernatant was discarded.

(2) The tube was taken off from the magnet stand, 0.3 mL of PBS was added and mixed. The tube was set on the magnet stand and left still for 1 minute, and then supernatant was discarded. The procedure in this (2) (cleaning) was carried out three times in total.

(3) 200 µL of PBS was added to the tube and streptavidin magnetic beads were resuspended in PBS, and thus cleaned streptavidin magnetic beads (200 µL) were obtained.

(4) 15 µL of the biotin-labeled polylysine peptide (Biotin-K4, Biotin-K8, or Biotin-K16) was added to the tube (100 µM).

(5) The substances in the tube were mixed together for 30 minutes at a room temperature so that the biotin-labeled polylysine peptide was brought into contact with the streptavidin magnetic beads, and thus the biotin-labeled polylysine peptide was bound to (i.e., caused to be supported by) the streptavidin magnetic beads.

(6) The tube was set on the magnet stand and left still for 1 minute, and then supernatant was discarded.

(7) A procedure (cleaning) similar to the procedure (2) was carried out three times in total.

(8) 50 µL of PBS was added to the tube and streptavidin magnetic beads were resuspended in PBS, and thus streptavidin magnetic beads on which the biotin-labeled polylysine peptide was supported (0.5 mg/50 µL) were obtained.

In this specification, the streptavidin magnetic beads on which the biotin-labeled polylysine peptide is supported is referred to as "polylysine-immobilized magnetic beads". In particular, in this specification, streptavidin magnetic beads on which Biotin-K4 is supported, streptavidin magnetic beads on which Biotin-K8 is supported, and streptavidin magnetic beads on which Biotin-K16 is supported are respectively referred to as "K4 immobilized magnetic beads", "K8 immobilized magnetic beads", and "K16 immobilized magnetic beads".

<2> Extraction and Purification of miRNA

Extraction and purification of miRNA were carried out with use of miRCURY RNA Isolation kit Cell & Plant (available from EXIQON). Specifically, a predetermined amount of lysis solution (as an extraction buffer) was added to (i) polylysine-immobilized magnetic beads (0.5 mg) or streptavidin magnetic beads (0.5 mg) to which exosomes were bound, (ii) a dissociation buffer (100 µL) containing exosomes after the dissociating step, or (iii) preprocessed serum supernatant (50 µL), the mixture was shaken for 5 minutes to dissolve exosomes, and miRNA was extracted. The tube was set on the magnet stand and left still for 1 minute to collect supernatant (miRNA fraction), and then purification of miRNA was carried out in accordance with a protocol of EXIQON. Ultimately, miRNA was collected in 50 µL of an elution buffer.

<3> Measurement of Exosome Amount

According to an embodiment of the present invention, an exosome amount was measured by quantitatively determining, with the qRT-PCR method, an amount of miR142-3p among miRNA collected in accordance with the method in <2> above. Note that miR142-3p is known to be specifically contained in exosomes.

The qRT-PCR method is a method in which (A) RNA (including miRNA) is first converted into complementary DNA (cDNA) by reverse transcription (RT), and then (B) an amount of converted cDNA is determined by real time PCR.

Specific methods in (A) and (B) above are as follows:
(A) Reverse transcription was carried out in accordance with a protocol of Life Technologies Corporation with use of TaqMan MicroRNA Reverse Transcription kit (available from Life Technologies Corporation) as an RT reaction reagent and an RT-primer of TaqMan MicroRNA Assays: hsa-miR-142-3p (Assay ID: 000464) (available from Life Technologies Corporation) as a primer.
(B) Real time PCR was carried out in accordance with a protocol of Life Technologies Corporation with use of TaqMan Universal Master Mix II, no UNG (available from Life Technologies Corporation) or TaqMan Fast Advanced Master Mix (available from Life Technologies Corporation) as a PCR reagent and a PCR-primer of TaqMan MicroRNA Assays: hsa-miR-142-3p (Assay ID: 000464) (available from Life Technologies Corporation) as a primer.

<4> Collection of Exosomes from Serum with Use of Polylysine-Immobilized Magnetic Beads As serum, Human Serum (available from Sigma-Aldrich) was used. The serum was centrifuged with a centrifugal separator at 10000 g for 10 minutes at 4° C., and thus components such as blood cells were precipitated. Serum supernatant was collected while taking care not to suck up precipitates. 0.1 mL of the serum supernatant which had been thus preprocessed was added to a 1.5 mL microtube, and 0.4 mL of PBS was added to the tube so as to dilute the serum supernatant. Thus, a serum solution (0.5 mL) was obtained.

Exosomes in the serum solution (0.5 mL) were collected with the following method.
(1) The K4 immobilized magnetic beads, the K8 immobilized magnetic beads, or the K16 immobilized magnetic beads (0.5 mg/50 µL) prepared in accordance with the method in the above <1> were added to the tube containing the serum solution (0.5 mL).
(2) The contents in the tube were mixed for 60 minutes at a room temperature so as to bring exosomes in the serum solution into contact with the polylysine-immobilized magnetic beads, and thus the exosomes were bound to the polylysine peptide. That is, in this step (2), a complex was formed which contained an exosome, the polylysine peptide (peptide), and the streptavidin magnetic beads (carrier).
(3) The tube was set on the magnet stand and left still for 1 minute, and then supernatant was discarded.
(4) The complex was cleaned through the following procedures: (4-1) The tube was taken off from the magnet stand, and 0.5 mL of PBS containing 0.01% of bovine serum albumin (BSA) (in this specification, also referred to as "PBS (+0.01% BSA)") was added to and mixed in the tube; (4-2) The tube was set on the magnet stand and left still for 1 minute, and then supernatant was discarded.
(5) The procedures in the above (4) (cleaning) were additionally carried out two times (i.e., three times in total), and thus polylysine-immobilized magnetic beads (0.5 mg) containing, as the complex, the exosomes in the serum (serum solution) was collected.

As a negative control, procedures similar to those in the above (1) through (5) were carried out with use of streptavidin magnetic beads (0.5 mg/50 µL) on which no biotin-labeled polylysine peptide was supported, and streptavidin magnetic beads (0.5 mg) to which exosomes in serum (serum solution) were bound were collected.

<5> Collection of Exosomes from Serum by Immunoprecipitation

As serum, Human Serum (available from Sigma-Aldrich) was used. The serum was centrifuged with a centrifugal separator at 10000 g for 10 minutes at 4° C., and thus components such as blood cells were precipitated. Serum supernatant was collected while taking care not to suck up precipitates. 0.1 mL of the serum supernatant which had been thus preprocessed was added to a 1.5 mL microtube, and 0.4 mL of PBS was added to the tube so as to dilute the serum supernatant. Thus, a serum solution (0.5 mL) was obtained.

As an antibody, Anti-CD9 antibody to which biotin was bound [CD9 Antibody (MEM-61) Biotin, available from Novus Biologicals] (hereinafter, referred to as "biotin-labeled Anti-CD9 antibody" or simply as "CD9 antibody") was used.

Exosomes in the serum solution (0.5 mL) were collected with the following method.
(1) 5 µL of a 1 mg/mL biotin-labeled Anti-CD9 antibody was added to the tube containing the serum solution (0.5 mL).
(2) The contents in the tube were mixed for 60 minutes at a room temperature so as to bring exosomes in the serum solution into contact with the CD9 antibody, and thus the exosomes were bound to the CD9 antibody.
(3) 50 µL (0.5 mg) of streptavidin magnetic beads were added to the tube of the above (2).
(4) The contents in the tube were mixed for 60 minutes at a room temperature so as to bring the CD9 antibody to which the exosomes had been bound into contact with the streptavidin magnetic beads, and thus the exosomes were bound to the streptavidin magnetic beads via the biotin-labeled Anti-CD9 antibody.
(5) The tube was set on the magnet stand and left still for 1 minute, and then supernatant was discarded.
(6) The streptavidin magnetic beads to which the exosomes had been bound via the CD9 antibody were cleaned through the following procedures: (6-1) The tube was taken off from the magnet stand, 0.5 mL of PBS (+0.01% BSA) was added and mixed; (6-2) The tube was set on the magnet stand and left still for 1 minute, and then supernatant was discarded.
(7) The procedures in the above (6) (cleaning) was additionally carried out two times (i.e., three times in total), and thus streptavidin magnetic beads (0.5 mg) to which the exosomes in the serum were bound via the CD9 antibody were collected.

<6> Preparation of Magnetic Beads Supporting Peptide (Poly L Lysine-Silica Magnetic Beads)

As a carrier, silica magnetic beads (available from MoBiTec, Magnetic silica beads S1.0) were used.

As a peptide, one of poly-L-lysine (molecular weight: 4,000-15,000) [available from Sigma-Aldrich] and poly-L-lysine solution (molecular weight: 150,000-300,000) [available from Sigma-Aldrich] was used. In this specification, both of those two types of poly-L-lysine are also referred to as "poly L lysine peptide". The poly-L-lysine (molecular weight: 4,000-15,000) was prepared to be 1.9 mg/mL with Milli-Q water (ultrapure water) and was used. The poly-L-lysine solution (molecular weight: 150,000-300,000) was sold as a 1 mg/mL aqueous solution, and was used as it was.

Figure 5:
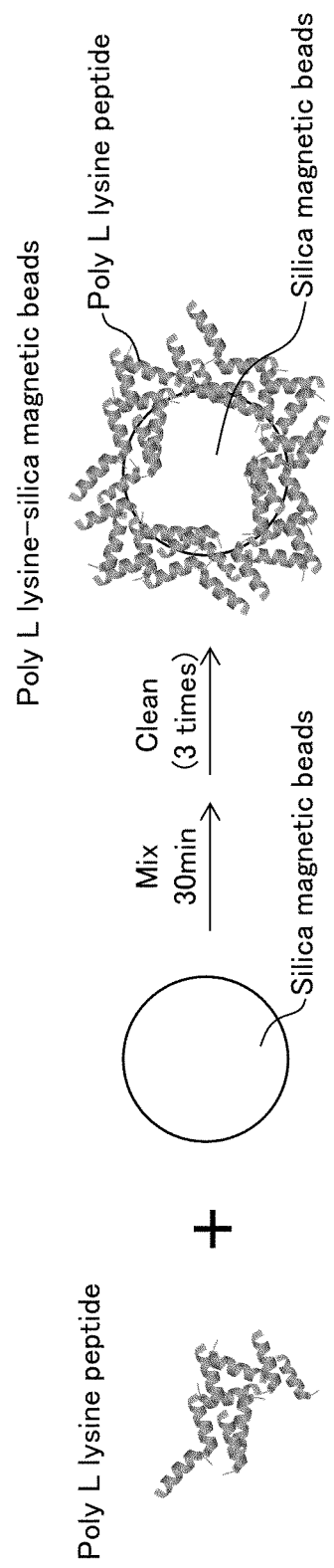
FIG. 5 is a view schematically illustrating procedures for preparing magnetic beads (poly L lysine-silica magnetic beads) on which a peptide is supported.

Schematic procedures for preparing magnetic beads (poly L lysine-silica magnetic beads) on which a peptide was supported are illustrated in FIG. 5. FIG. 5 is a view schematically illustrating procedures for preparing magnetic beads (poly L lysine-silica magnetic beads) on which a peptide is supported. Specifically, poly L lysine-silica magnetic beads were prepared with the following method as magnetic beads on which a peptide was supported.

(1) 20 μL (0.2 mg) of silica magnetic beads were added to a 1.5 mL microtube, then the tube was set on a magnet stand and left still for 1 minute, and then supernatant was discarded.

(2) The tube was taken off from the magnet stand, 0.2 mL of PBS was added and mixed. The tube was set on the magnet stand and left still for 1 minute, and then supernatant was discarded. The procedure in this (2) (cleaning) was carried out three times in total.

(3) 50 μL of PBS was added to the tube and silica magnetic beads were resuspended in PBS, and thus cleaned silica magnetic beads (50 μL) were obtained.

(4) 97 μL of poly-L-lysine (molecular weight: 4,000-15,000) was added to the tube, and 153 μL of PBS was further added so that a solution in the tube becomes 300 μL. 60 μL of poly-L-lysine (molecular weight: 150,000-300,000) was added to another tube, and 190 μL of PBS was further added so that a solution in that tube becomes 300 μL.

(5) The contents of the tube were mixed for 30 minutes at a room temperature, and thus the poly L lysine peptide was bound to (i.e., immobilized on) the silica magnetic beads.

(6) The tube was set on the magnet stand and left still for 1 minute, and then supernatant was discarded.

(7) The tube was taken off from the magnet stand, 0.3 mL of PBS was added and mixed. The tube was set on the magnet stand and left still for 1 minute, and then supernatant was discarded. The procedure in this (7) (cleaning) was carried out three times in total.

(8) 50 μL of PBS was added to the microtube and silica magnetic beads were resuspended in PBS, and thus silica magnetic beads (0.2 mg/50 μL) on which the poly L lysine peptide was supported were obtained as magnetic beads supporting the peptide.

In this specification, the silica magnetic beads on which the poly L lysine peptide is supported is also referred to as "poly L lysine-silica magnetic beads". Moreover, in this specification, silica magnetic beads on which the poly-L-lysine (molecular weight: 4,000-15,000) [available from Sigma-Aldrich] is supported are also referred to as "poly L lysine-silica magnetic beads A" and silica magnetic beads on which the poly-L-lysine solution (molecular weight: 150,000-300,000) [available from Sigma-Aldrich] is supported are also referred to as "poly L lysine-silica magnetic beads B".

<7> Collection of Exosomes from Serum with Use of Poly L Lysine-Silica Magnetic Beads As serum, Human Serum (available from Sigma-Aldrich) was used. The serum was centrifuged with a centrifugal separator at 10000 g for 10 minutes at 4° C., and thus components such as blood cells were precipitated.

Serum supernatant was collected while taking care not to suck up precipitates. 0.1 mL of the serum supernatant which had been thus preprocessed was added to a 1.5 mL microtube, and 0.4 mL of PBS was added to the tube so as to dilute the serum supernatant. Thus, a serum solution (0.5 mL) was obtained.

Exosomes in the serum solution (0.5 mL) were collected with the following method.

(1) The poly L lysine-silica magnetic beads A or B (0.2 mg/50 μL) prepared in accordance with the method in the above <6> were added to the tube containing the serum solution (0.5 mL).

(2) The contents in the tube were mixed for 60 minutes at a room temperature so as to bring exosomes in the serum solution into contact with the poly L lysine-silica magnetic beads, and thus the exosomes were bound to the poly L lysine peptide. That is, in this step (2), a complex was formed which contained an exosome, the poly L lysine peptide (peptide), and the silica magnetic beads (carrier).

(3) The tube was set on the magnet stand and left still for 1 minute, and then supernatant was discarded.

(4) The tube was taken off from the magnet stand, 0.5 mL of PBS (+0.01% BSA) was added to and mixed in the tube. The tube was set on the magnet stand and left still for 1 minute, and then supernatant was discarded. The procedure in this (4) (cleaning) was carried out three times in total, and thus poly L lysine-silica magnetic beads A or B (0.2 mg) containing, as the complex, the exosomes in the serum (serum solution) were collected.

[Test Example 1] Comparison of Collected Amounts of Exosomes, and Influence of the Number of Polylysines on the Exosome Collection Amount A collected amount of exosomes collected with use of the peptide of the present invention was compared with a collected amount of exosomes obtained by conventional immunoprecipitation. Moreover, influence of the number of lysines (specifically, a chain length of polylysine) contained in the peptide of the present invention on the collected amount of exosomes was also evaluated. Measurement and comparison of the collected amounts of exosomes were carried out by quantitatively determining an amount of miRNA (miR142-3p) contained in exosomes. Schematic experimental procedures in Test Example 1 are shown in FIG. 1. FIG. 1 is a view schematically illustrating experimental procedures in Test Example 1.

Collection of exosomes with use of the peptide of the present invention was carried out in accordance with the method of the above <4>. Here, as polylysine-immobilized magnetic beads, the K4 immobilized magnetic beads, the K8 immobilized magnetic beads, or the K16 immobilized magnetic beads were used. As a negative control, streptavidin magnetic beads supporting no biotin-labeled polylysine peptide (i.e., streptavidin magnetic beads only) were used. As a comparison, collection of exosomes by conventional immunoprecipitation was carried out in accordance with the method of the above <5>.

miRNA contained in each of collected exosomes was extracted and purified in accordance with the method of the above <2>. An amount of a lysis solution used was 350 μL. For each purified miRNA, an amount of miR142-3p was quantitatively determined by qRT-PCR in accordance with the method of the above <3>, and thus an exosome amount was measured. Based on Ct values obtained by qRT-PCR, relative concentrations were calculated and shown in Table 1, while setting a concentration of miR142-3p obtained from exosomes collected by immunoprecipitation as 1. In Table 1, the Ct value indicates the number of cycles at which a PCR product reaches a certain amount, and ΔCt indicates a value obtained by subtracting a Ct value of a criterion example from a Ct value of each example. Specifically, ΔCt indicates a value obtained by subtracting the Ct value of immunoprecipitation from the Ct value of each example.

TABLE 1

|  | Immuno-precipitation | Magnetic beads only | K4 immobilized magnetic beads | K8 immobilized magnetic beads | K16 immobilized magnetic beads |
| --- | --- | --- | --- | --- | --- |
| Ct value | 32.42 | 36.98 | 34.42 | 28.84 | 29.79 |
| ΔCt | 1 | 4.56 | 2 | −3.58 | −2.63 |
| Relative concentration ($2^{-\Delta Ct}$) | 1 | 0.04 | 0.25 | 11.96 | 6.19 |

From the results shown in Table 1, it was found that relative concentrations of miR142-3p in cases where the K4 immobilized magnetic beads, the K8 immobilized magnetic beads, and the K16 immobilized magnetic beads were used were 0.25, 11.96, and 6.19, respectively. A relative concentration of miR142-3p in the case where streptavidin magnetic beads only (in Table 1, indicated as "Magnetic beads only") were used was 0.04, and it was thus found that exosomes were hardly bound to the streptavidin magnetic beads themselves. From this, it was found that, in a case where exosomes were collected with use of the peptide containing four or more lysines (polylysine peptide polylysine), exosomes bound specifically to the polylysine peptide and thus the exosomes could be collected. Moreover, it was found that, in a case where exosomes were collected with use of the peptide containing eight or more lysines, exosomes could be collected at a high yield which was 6 to 12 times greater than that of the case where exosomes were collected by immunoprecipitation. That is, it was found that exosomes could be collected extremely efficiently by using the peptide containing eight or more lysines, as compared with the conventional immunoprecipitation.

Note that, it was found that, even in the case where the peptide containing four or more lysines was used, exosomes could be collected although a yield was low, i.e., approximately ¼ as compared with the case where exosomes were collected by immunoprecipitation. Since exosomes could be collected from the sample even in the case where the peptide containing four or more lysines was used, it can be said that the isolation method of the present invention can be carried out by that case.

[Test Example 2] Study 1 of Dissociation Buffer

Figure 2:
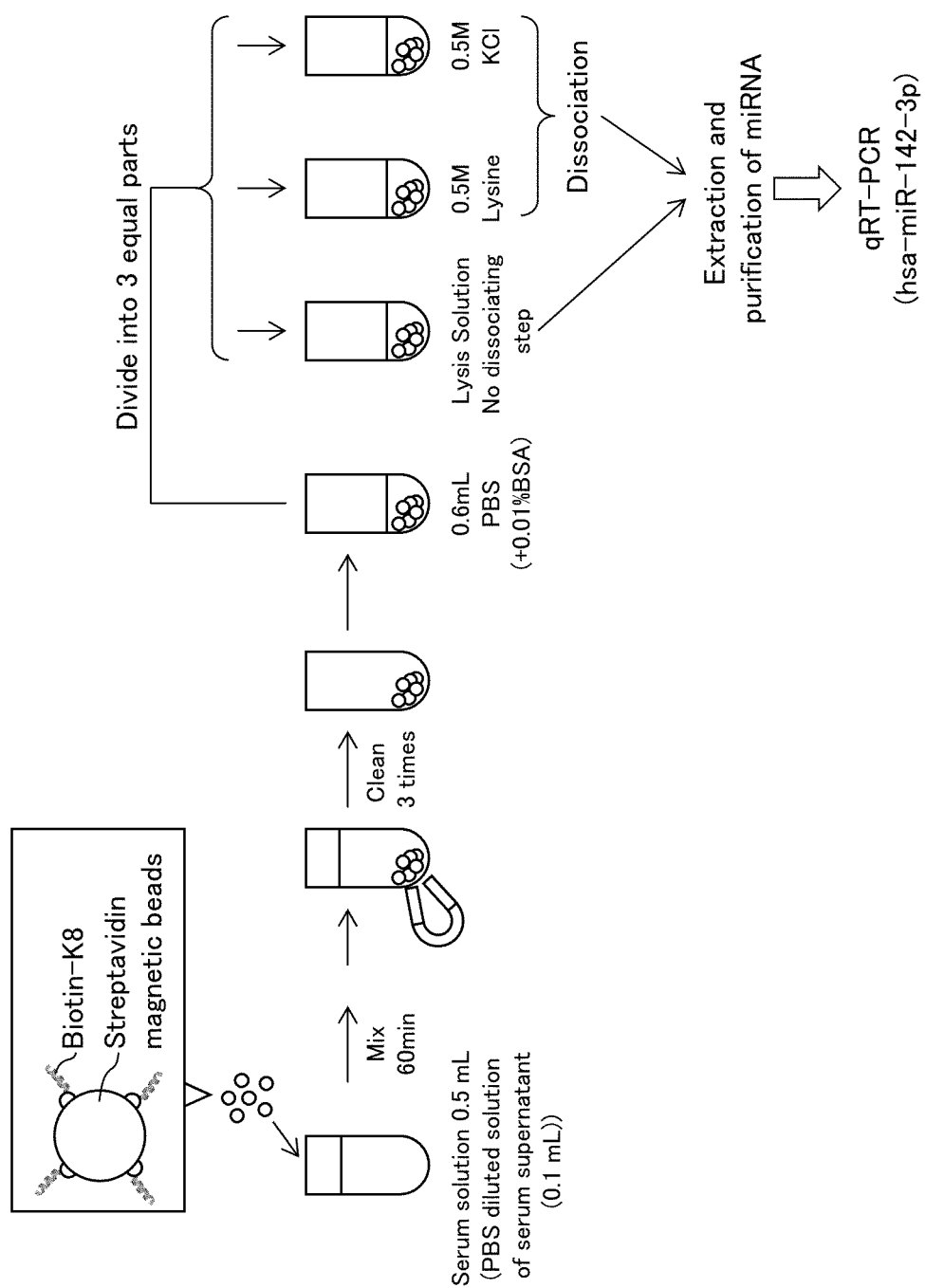
FIG. 2 is a view schematically illustrating experimental procedures in Test Example 2.

In a case where exosomes themselves are to be utilized, it is necessary to isolate exosomes from magnetic beads (complex) in an intact state (or in a substantially intact state). In the case of the conventionally known immunoprecipitation, a protein of a surface of exosome binds to an antibody, and it is therefore necessary to separate exosomes from magnetic beads by denaturing the antibody with use of a protein denaturant or the like. In particular, the lysis solution denatures the protein on the surface of exosome and further has a function to dissolve the exosome itself. If it is possible to dissociate exosomes from magnetic beads under gentle conditions, it may be possible to isolate exosomes in an intact state (or in a substantially intact state) without denaturation of the protein. In view of this, in this test example, whether or not exosomes can be dissociated from magnetic beads under gentle conditions was studied. Schematic experimental procedures in Test Example are shown in FIG. 2. FIG. 2 is a view schematically illustrating experimental procedures in Test Example 2.

First, exosomes were collected from serum with use of the K8 immobilized magnetic beads in accordance with the method of the above <4>. The collected exosomes were divided into three equal parts and, for one of the three parts, exosomes were dissolved with use of a lysis solution to extract miRNA (control). For the rest of two parts, exosomes were dissociated from the complexes with use of a dissociation buffer.

The specific experiment method is as follows:
(1) 0.6 mL of PBS (+0.01% BSA) was added to a tube containing the K8 immobilized magnetic beads (0.5 mg) that contained exosomes as complexes, and thus the K8 immobilized magnetic beads were resuspend in the PBS.
(2) A suspension of 0.6 mL of the K8 immobilized magnetic beads obtained in the above (1) was divided into three equal parts, and the three parts were poured into respective three 1.5 mL microtubes by 0.2 mL for each.
(3) Each of the three tubes was set on a magnet stand and left still for 1 minute, and then supernatant was discarded. Here, for one of the three tubes, exosomes were dissolved with use of a lysis solution (350 μL) in accordance with the method of the above <2>, and thus miRNA was extracted (control).
(4) To the two tubes, a lysine solution [50 mM Tris-HCl (pH 7.4), 0.5 M Lysine] and a KCl solution [50 mM Tris-HCl (pH 7.4), 0.5 M KCl] were respectively added as dissociation buffers in an amount of 100 μL for each, and then the tubes were shaken for 5 minutes. Thus, exosomes were dissociated from the complexes, and the dissociation buffer (100 μL) was isolated to isolate exosomes.

miRNA contained in each of isolated exosomes was extracted and purified in accordance with the method of the above <2>. An amount of a lysis solution used was 350 μL. For each purified miRNA, an amount of miR142-3p was quantitatively determined by qRT-PCR in accordance with the method of the above <3>, and thus an exosome amount was measured. Based on Ct values obtained by qRT-PCR, relative concentrations were calculated and shown in Table 2, while setting, as 1, a concentration of miR142-3p (i.e., concentration of control) obtained by dissolving exosomes with use of a lysis solution without using a dissociation buffer.

TABLE 2

|  | Control | 0.5M Lysine | 0.5M KCl |
| --- | --- | --- | --- |
| Ct value | 30.2 | 31.49 | 30.2 |
| Relative concentration ($2^{-\Delta Ct}$) | 1 | 0.36 | 1 |

From the results shown in Table 2, it was found that the relative concentrations of miR142-3p in cases where the lysine solution and the KCl solution were used in dissociation were 0.36 and 1, respectively. It was thus found that, in both the cases where the lysine solution and the KCl solution were used as dissociation buffers, exosomes could be dissociated from the complexes. Note, however, that, in the case where the lysine solution was used as a dissociation buffer, the relative concentration of miR142-3p was lower as compared with the case where the lysis solution was used. Meanwhile, in the case where the KCl solution was used, the amount of isolated exosomes was equal to that of the case where miRNA was extracted by dissolving, with use of the lysis solution, exosomes which had been bound to the K8 immobilized magnetic beads. As such, it was found that the KCl solution could dissociate, from the complexes, all exosomes which had been bound to the K8 immobilized magnetic beads in the complexes. Unlike the lysis solution, the KCl solution does not influence a membrane structure of exosome and a structure of protein existing in the membrane. That is, in the case where the KCl solution was used, it was possible to isolate exosomes under a gentle condition with respect to the membrane structure of exosome and the structure of protein existing in the membrane, as compared with the case where the lysis solution was used. As such, in the case where the KCl solution was used, it was highly possible that exosomes were isolated in an intact state (or in a substantially intact state).

Note that, for exosomes collected by the conventional immunoprecipitation (i.e., collected in accordance with the method of the above <5>), exosomes could not be dissociated from the complexes in both cases where the lysine solution and the 0.5 M KCl solution were used as dissociation buffers. That is, the immunoprecipitation could not isolate exosomes in an intact state (or a substantially intact state).

[Test Example 3] Study 2 of Dissociation Buffer

Figure 3:
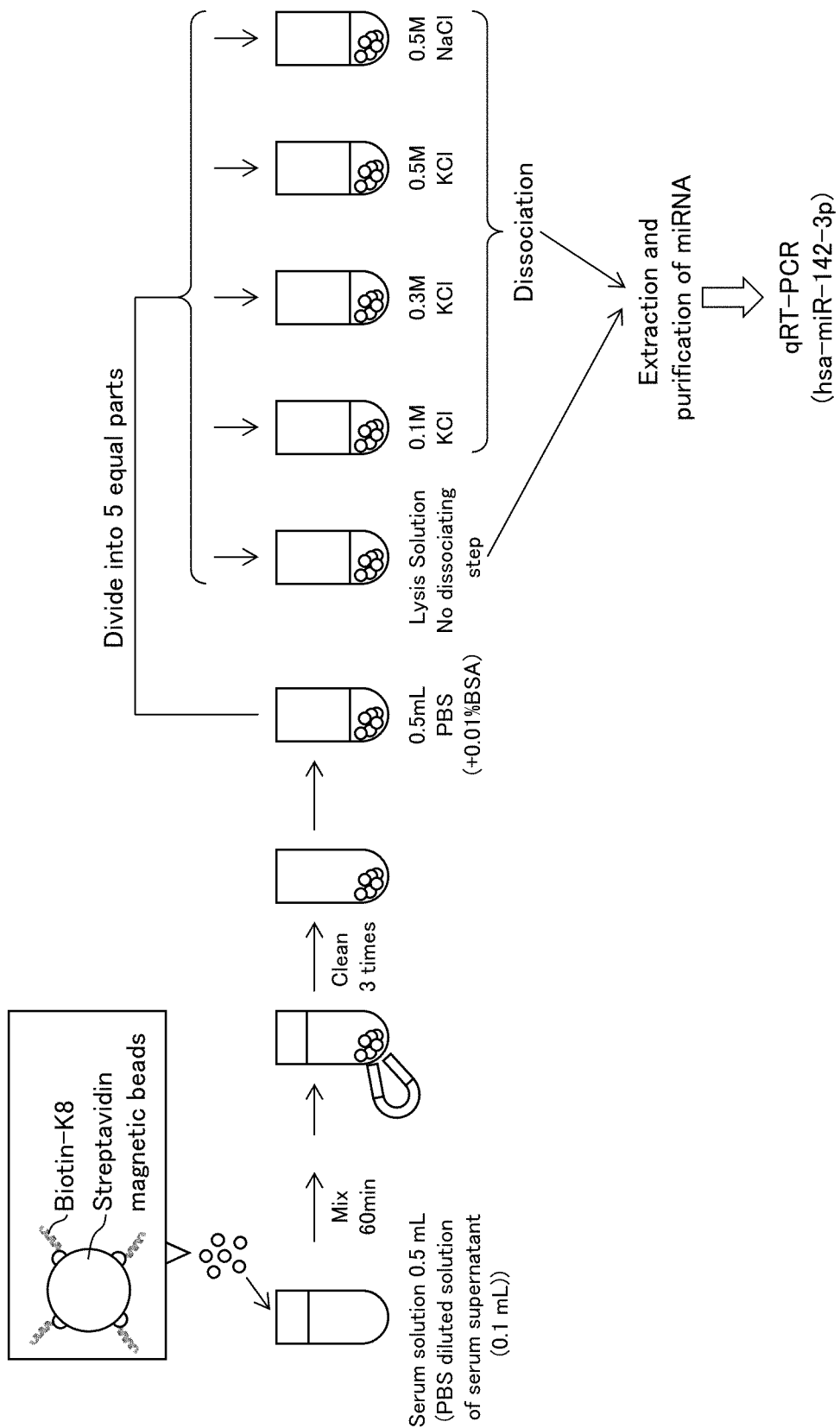
FIG. 3 is a view schematically illustrating experimental procedures in Test Example 3 in which a dissociation buffer containing monovalent metal cations is used.
Figure 4:
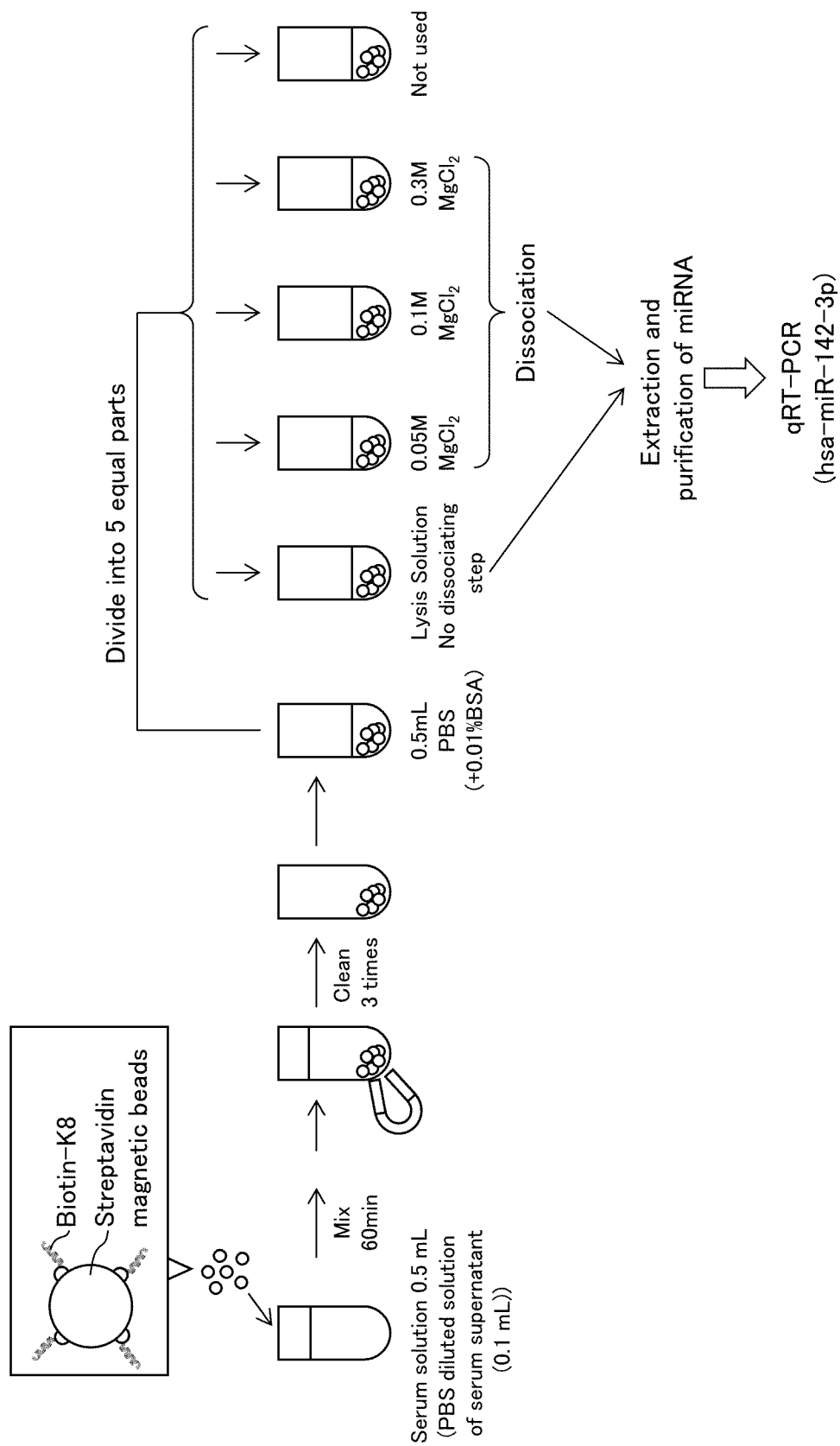
FIG. 4 is a view schematically illustrating experimental procedures in Test Example 3 in which a dissociation buffer containing bivalent metal cations is used.

From the results of Test Example 2, it was found that exosomes could be dissociated from the complexes by using the KCl solution, which contained potassium ions (i.e., metal cations), as a dissociation buffer. Under the circumstances, amounts of exosomes isolated from complexes with use of dissociation buffers containing various types of metal cations at various concentrations were evaluated. In regard to the dissociation buffers, a KCl solution and an NaCl solution were used as dissociation buffers containing monovalent metal cations, and an $MgCl_2$ solution was used as a dissociation buffer containing bivalent metal cations. Schematic experimental procedures in Test Example 3 are shown in FIG. 3 and FIG. 4. FIG. 3 is a view schematically illustrating experimental procedures in Test Example 3 in which a dissociation buffer containing monovalent metal cations is used. FIG. 4 is a view schematically illustrating experimental procedures in Test Example 3 in which a dissociation buffer containing bivalent metal cations is used.

First, exosomes were collected from serum with use of the K8 immobilized magnetic beads in accordance with the method of the above <4>. The collected exosomes were divided into five equal parts and, for one of the five parts, exosomes were dissolved with use of a lysis solution to extract miRNA (control). For the rest of four parts, exosomes were dissociated from the complexes with use of dissociation buffers. The specific method is as follows:

(1) 0.5 mL of PBS (+0.01% BSA) was added to a tube containing the K8 immobilized magnetic beads (0.5 mg) that contained exosomes as complexes, and thus the K8 immobilized magnetic beads were resuspend in the PBS.

(2) A suspension of 0.5 mL of the K8 immobilized magnetic beads obtained in the above (1) was poured into five 1.5 mL microtubes by 0.1 mL (K8 immobilized magnetic beads: 0.1 mg) for each.

(3) Each of the five tubes was set on a magnet stand and left still for 1 minute, and then supernatant was discarded. Here, for one of the five tubes, exosomes were dissolved with use of a lysis solution (350 μL) in accordance with the method of the above <2>, and thus miRNA was extracted and purified (control).

(4) To the rest of four tubes, KCl solutions respectively containing 0.1 M KCl, 0.3 M KCl, and 0.5 M KCl [10 mM Tris-HCl (pH 7.4) with the concentrations (M) of KCl] and an NaCl solution [10 mM Tris-HCl (pH 7.4), 0.5 M NaCl] were added as dissociation buffers in an amount of 100 μL for each, and then the tubes were shaken for 5 minutes. Thus, exosomes were dissociated from the complexes, and the dissociation buffer (100 μL) was isolated to isolate exosomes. As dissociation buffers, a 0.1 M KCl solution containing 0.1 M of KCl, a 0.3 M KCl solution containing 0.3 M of KCl, a 0.5 M KCl solution containing 0.5 M of KCl, and a 0.5 M NaCl solution containing 0.5 M of NaCl were used. Furthermore, exosomes were isolated in manners similar to those described in the above (1) through (4), except that a 0.05 M $MgCl_2$ solution containing 0.05 M of $MgCl_2$, a 0.1 M $MgCl_2$ solution containing 0.1 M of $MgCl_2$, and a 0.3 M $MgCl_2$ solution containing 0.3 M of $MgCl_2$ were used as dissociation buffers (see FIG. 4).

miRNA contained in each of isolated exosomes was extracted and purified in accordance with the method of the above <2>. An amount of a lysis solution used was 350 μL. For each purified miRNA, an amount of miR142-3p was quantitatively determined by qRT-PCR in accordance with the method of the above <3>, and thus an exosome amount was measured. Based on Ct values obtained by qRT-PCR, relative concentrations were calculated and shown in Tables 3 and 4, while setting, as 1, a concentration of miR142-3p (i.e., concentration of control) obtained by dissolving exosomes with use of a lysis solution without using a dissociation buffer.

TABLE 3

|  | Control | 0.1M KCl | 0.3M KCl | 0.5M KCl | 0.5M NaCl |
|---|---|---|---|---|---|
| Ct value | 32.46 | 37.08 | 33.2 | 32.46 | 32.64 |
| Relative concentration ($2^{-\Delta Ct}$) | 1 | 0.04 | 0.60 | 1 | 0.88 |

TABLE 4

|  | Control | 0.05M $MgCl_2$ | 0.1M $MgCl_2$ | 0.3M $MgCl_2$ |
|---|---|---|---|---|
| Ct value | 30.67 | 32.33 | 31.48 | 30.76 |
| Relative concentration ($2^{-\Delta Ct}$) | 1 | 0.32 | 0.57 | 0.94 |

From the results shown in Table 3, it was found that the relative concentrations of miR142-3p in cases where the 0.1 M KCl solution, the 0.3 M KCl solution, the 0.5 M KCl solution, and the 0.5 M NaCl solution were used were 0.04, 0.60, 1, and 0.88, respectively, with respect to the concentration 1 of the control. It was thus found that, in a case where the KCl solution which was a monovalent metal cation solution was used as the dissociation buffer in this test example, a sufficient amount of exosomes could be dissociated from the complexes, provided that the KCl concentration in the KCl solution was 0.3 M or more. Moreover, it was shown that the amount of exosomes isolated by using the 0.5 M KCl solution as the dissociation buffer was equal to that of the case of control. Further, it was found that, in the case where the NaCl solution which was a monovalent metal cation solution as with the KCl solution was used (specifically, in the case where the 0.5 M NaCl solution was used) as the dissociation buffer, 88% of exosomes could be dissociated from the complexes.

From the results shown in Table 4, it was found that the relative concentrations of miR142-3p in cases where the 0.05 M MgCl solution, the 0.1 M $MgCl_2$ solution, and the 0.3 M $MgCl_2$ solution were used were 0.32, 0.57, and 0.94, respectively, with respect to the concentration 1 of the control. It was thus found that, in the case where the $MgCl_2$ solution which was a bivalent metal cation solution was used as the dissociation buffer in this test example, exosomes could be dissociated from the complexes, even though the $MgCl_2$ concentration in the $MgCl_2$ solution was 0.05 M. Moreover, it was found that, in a case where the $MgCl_2$ solution having an $MgCl_2$ concentration of 0.1 M or more was used as the dissociation buffer, a sufficient amount of exosomes could be dissociated from the complexes. Further, it was found that, in the case where the 0.3 M $MgCl_2$ solution was used as the dissociation buffer, 94% of exosomes could be dissociated from the complexes.

Unlike the lysis solution, the NaCl solution and the $MgCl_2$ solution do not influence a membrane structure of exosome and a structure of protein existing in the membrane. That is, in the case where the NaCl solution and the $MgCl_2$ solution were used, as with the case of the KCl solution, it was possible to isolate exosomes under gentle conditions with respect to the membrane structure of exosome and the structure of protein existing in the membrane, as compared with the case where the lysis solution was used. As such, as with the case of the KCl solution, in the cases where the NaCl solution and the $MgCl_2$ solution were used also, it was highly possible that exosomes were isolated in an intact state (or in a substantially intact state).

Figure 6:
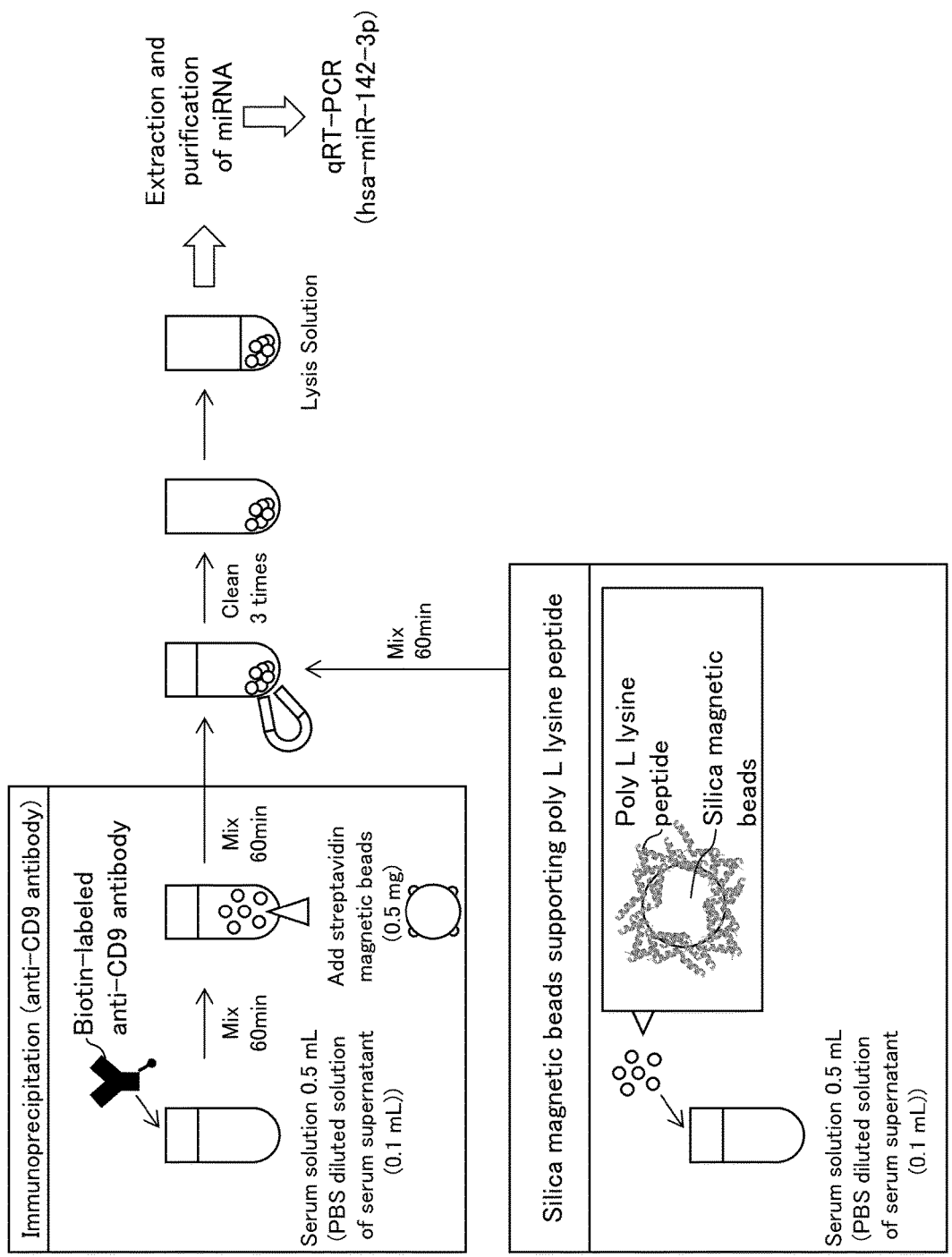
FIG. 6 is a view schematically illustrating experimental procedures in Test Example 4.

[Test Example 4] Collection of Exosomes from Serum with Use of Poly L Lysine-Silica Magnetic Beads A collected amount of exosomes collected from serum by using, as the peptide, commercially available general long-chain polylysine (such as poly-L-lysine) and by using silica as the carrier was compared with a collected amount of exosomes obtained by conventional immunoprecipitation. Schematic experimental procedures in Test Example 4 are shown in FIG. 6. FIG. 6 is a view schematically illustrating experimental procedures in Test Example 4. The specific method is as follows:

With use of the poly L lysine-silica magnetic beads A or B prepared in accordance with the method of the above <6>, exosomes were collected from serum in accordance with the method of the above <7>.

As a comparison, collection of exosomes by conventional immunoprecipitation was carried out in accordance with the method of the above <5>.

miRNA contained in each of collected exosomes was extracted and purified in accordance with the method of the above <2>. An amount of a lysis solution used was 200 μL. For each purified miRNA, an amount of miR142-3p was quantitatively determined by qRT-PCR in accordance with the method of the above <3>, and thus an exosome amount was measured. Based on Ct values obtained by qRT-PCR, relative concentrations were calculated and shown in Table 5, while setting a concentration of miR142-3p obtained from exosomes collected by immunoprecipitation as 1. In Table 5, a molecular weight of polylysine indicates a molecular weight of polylysine contained in the commercially available long-chain polylysine (poly-L-lysine) used in preparation of the poly L lysine-silica magnetic beads.

TABLE 5

| | Immuno-precipitation | Poly L lysine-silica magnetic beads A | Poly L lysine-silica magnetic beads B |
|---|---|---|---|
| Molecular weight of polylysine | — | 4,000-15,000 | 150,000-300,000 |
| Ct value | 32.42 | 31.69 | 31.24 |
| Relative concentration ($2^{-\Delta Ct}$) | 1 | 1.66 | 2.27 |

From the results of Table 5, it was found that the relative concentrations of miR142-3p in cases where poly L lysine-silica magnetic beads A and B were 1.66 and 2.27, respectively. From this, it was found that exosomes could be collected from serum even in the case where the commercially available general long-chain polylysine (such as poly-L-lysine) was used as the peptide and silica was used as the carrier. Moreover, in this case, exosomes could be collected at higher yields, i.e., 1.6 to 2.3 times greater than the case where exosomes were collected by immunoprecipitation. It was thus found that exosomes could be extremely efficiently collected, as compared with the conventional method.

Figure 7:
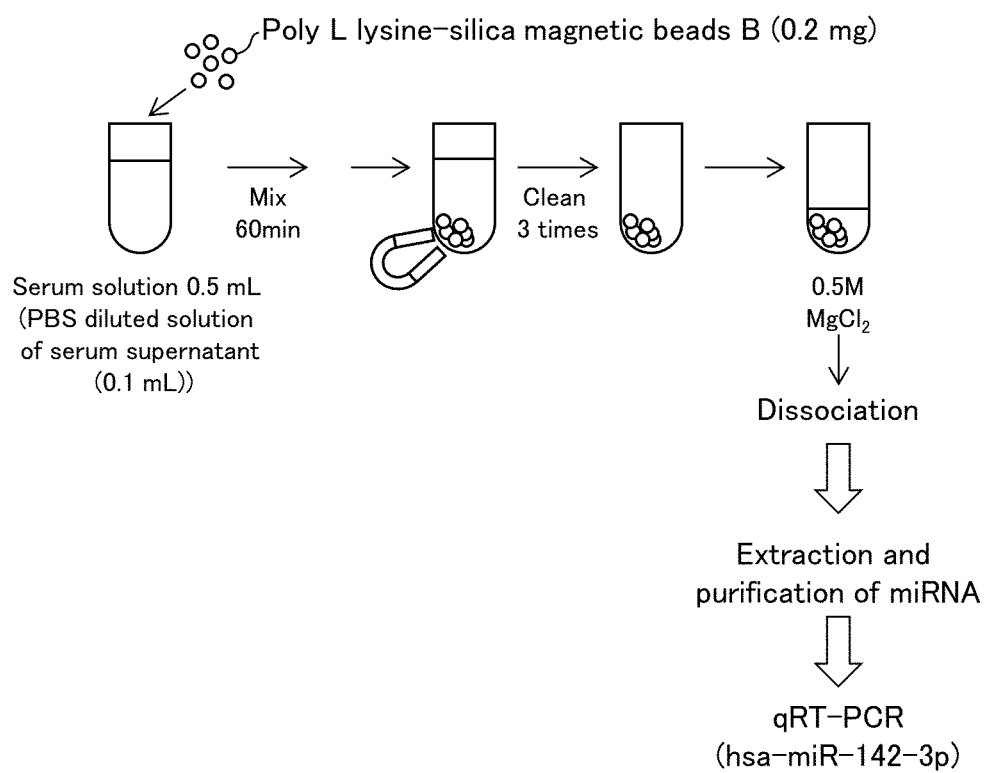
FIG. 7 is a view schematically illustrating experimental procedures in Test Example 5.

[Test Example 5] Isolation of Exosomes from Serum with Use of Poly L Lysine-Silica Magnetic Beads Amounts of exosomes isolated from complexes containing exosomes in serum were evaluated for cases where dissociation buffers were used. Schematic experimental procedures in Test Example 5 are shown in FIG. 7. FIG. 7 is a view schematically illustrating experimental procedures in Test Example 5. The specific method is as follows: The specific method is as follows:

First, exosomes were collected from serum with use of the poly L lysine-silica magnetic beads B in accordance with the method of the above <7>.

Next, to a tube containing the poly L lysine-silica magnetic beads B (0.2 mg) containing exosomes as complexes, an $MgCl_2$ solution containing 0.5 M of $MgCl_2$ [10 mM Tris-HCl (pH 7.4), 0.5 M $MgCl_2$] was added as a dissociation buffer in an amount of 100 μL, and then the tube was shaken for 5 minutes. Thus, exosomes were dissociated from the complexes, and the dissociation buffer (100 μL) was isolated to isolate exosomes.

After that, miRNA contained in isolated exosomes was extracted and purified in accordance with the method of the above <2>. An amount of a lysis solution used was 350 μL. For each purified miRNA, an amount of miR142-3p was quantitatively determined by qRT-PCR in accordance with the method of the above <3>, and thus an exosome amount was measured.

For miRNA obtained in [Test Example 4], an amount of miR142-3p was quantitatively determined by qRT-PCR as a control, and thus an exosome amount was measured.

Based on a Ct value obtained by qRT-PCR, a relative concentration in the case of isolating with use of the dissociation buffer was calculated and shown in Table 6, while setting, as 1, a concentration of miR142-3p which was the control.

TABLE 6

| | Control | 0.5M MgCl$_2$ |
|---|---|---|
| Ct value | 32.43 | 33.00 |
| Relative concentration ($2^{-\Delta Ct}$) | 1 | 0.67 |

From the results shown in Table 6, it was found that the relative concentration of miR142-3p in the case where the dissociation buffer was used was 0.67, with respect to the concentration 1 of the control. From this, it was found that, in the case where the MgCl$_2$ solution was used as the dissociation buffer, exosomes could be dissociated from the complexes. As above described, in the case where the MgCl$_2$ solution was used, it was possible to isolate exosomes under extremely gentle conditions with respect to the membrane structure of exosome and the structure of protein existing in the membrane, as compared with the case where the lysis solution was used. As such, in the case where the MgCl$_2$ solution was used, it was highly possible that exosomes were isolated in an intact state (or in a substantially intact state).

[Test Example 6] Evaluation of Degree of Exosome Purification

A degree of exosome purification in a case where exosomes were isolated from serum with use of the isolation method of the present invention was evaluated, while using a degree of removal of contaminating protein in serum as an indicator.

Figure 8:
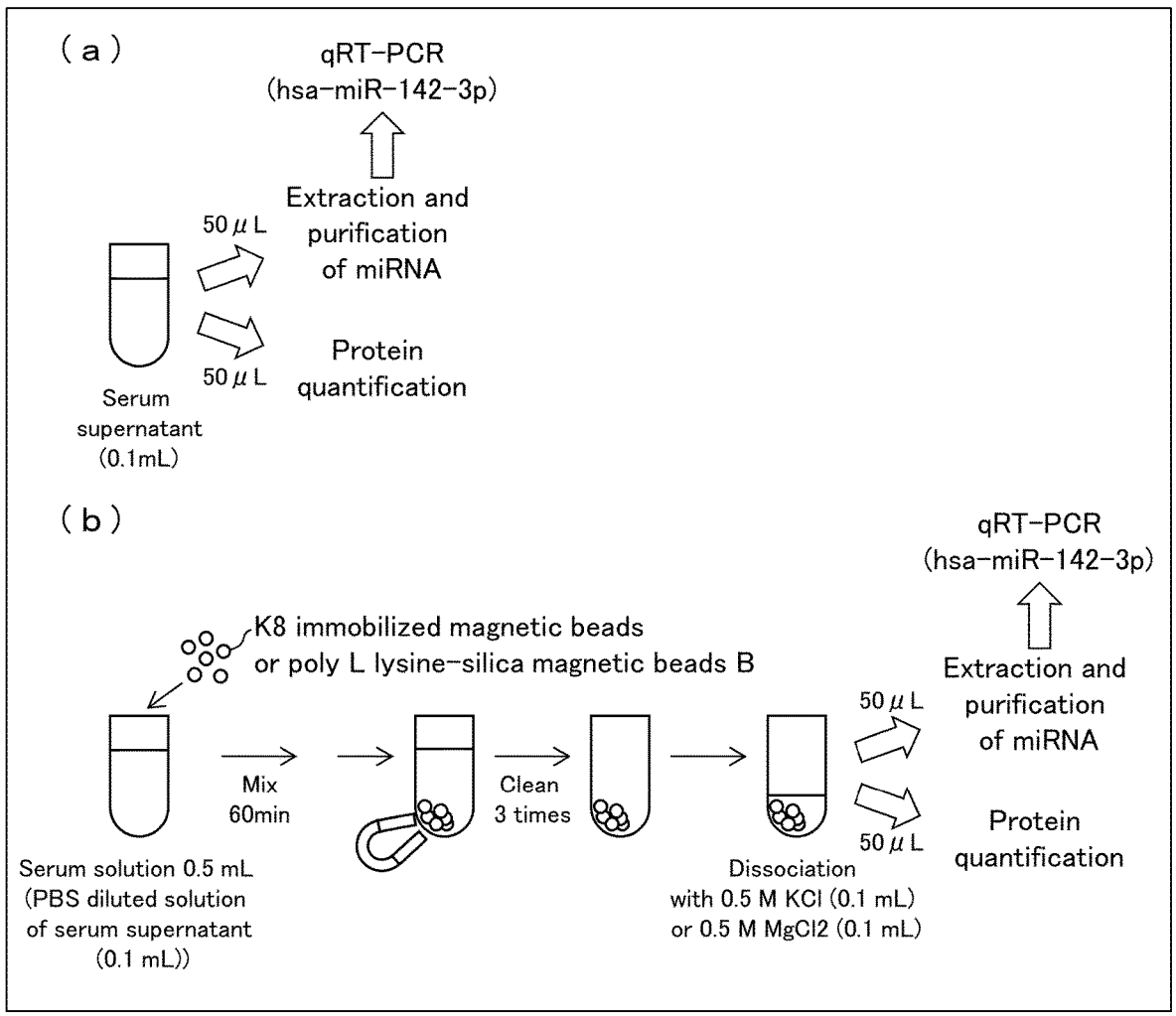
FIG. 8 is a view schematically illustrating experimental procedures in Test Example 6. (a) of FIG. 8 is a view schematically illustrating experimental procedures in Test Example 6 for measuring a protein concentration and an exosome amount in serum. (b) of FIG. 8 is a view schematically illustrating experimental procedures in Test Example 6 for measuring a protein concentration and an exosome amount in a dissociation buffer.

As serum, Human Serum (available from Sigma-Aldrich) was used. First, a concentration of protein and an amount of exosomes in serum were measured, and thus a protein concentration and an exosome amount before isolation were obtained. (a) of FIG. 8 shows schematic experimental procedures in Test Example 6 for measuring a protein concentration and an exosome amount in serum. The specific procedures are as follows: FIG. 8 is a view schematically illustrating experimental procedures in Test Example 6. (a) of FIG. 8 is a view schematically illustrating experimental procedures in Test Example 6 for measuring a protein concentration and an exosome amount in serum.

(1) The serum was centrifuged with a centrifugal separator at 10000 g for 10 minutes at 4° C., and thus components such as blood cells were precipitated.

(2) Serum supernatant was collected while taking care not to suck up precipitates.

(3) 0.1 mL of the serum supernatant which had been thus preprocessed was added to a 1.5 mL microtube.

(4) The protein concentration was measured with use of 50 μL out of 0.1 mL of the serum supernatant in the tube. The measurement of the protein concentration was carried out with use of Micro BCA Protein assay kit (available from Thermo Fisher Scientific K.K.).

(5) miRNA was extracted and purified in accordance with the method of the above <2> with use of the rest 50 μL of the serum supernatant. An amount of a lysis solution used was 350 μL.

(6) The purified miRNA, an amount of miR142-3p was quantitatively determined by qRT-PCR in accordance with the method of the above <3>, and thus an exosome amount in serum was measured.

Table 7 shows the protein concentration obtained in the above (4) and the exosome amount obtained in the above (6) as a protein concentration before isolation and an exosome amount before isolation, respectively.

Next, exosomes were isolated from serum with the method for isolating an exosome in accordance with an embodiment of the present invention, and then a concentration of protein and an amount of exosomes in the dissociation buffer were measured, and thus a protein concentration and an exosome amount after isolation were obtained. (b) of FIG. 8 shows schematic experimental procedures in Test Example 6 for measuring a protein concentration and an exosome amount in the dissociation buffer. (b) of FIG. 8 is a view schematically illustrating experimental procedures in Test Example 6 for measuring a protein concentration and an exosome amount in a dissociation buffer. The specific procedures are as follows:

(7) 0.1 mL of the serum supernatant which had been obtained in the above (2) and preprocessed was added to a 1.5 mL microtube, and 0.4 mL of PBS was added to the tube so as to dilute the serum supernatant. Thus, a serum solution (0.5 mL) was obtained. The serum solutions (0.5 mL each) were prepared in respective two tubes.

(8) With use of one of the two serum solutions (0.5 mL each), exosomes were collected from serum with use of the K8 immobilized magnetic beads in accordance with the method of the above <4>. Moreover, with use of the other one of the two serum solutions (0.5 mL each), exosomes were collected from serum with use of the poly L lysine-silica magnetic beads B in accordance with the method of the above <7>. Here, the polylysine-immobilized magnetic beads and the poly L lysine-silica magnetic beads B which contained exosomes as complexes were cleaned with PBS instead of PBS (+0.01% BSA).

(9) 100 μL of a KCl solution [10 mM Tris-HCl (pH 7.4), 0.5 M KCl] was added as a dissociation buffer to a tube containing the K8 immobilized magnetic beads (0.5 mg) that contained exosomes as complexes among the tubes obtained in the above (8). Then, the tube was shaken for 5 minutes, and thus exosomes were dissociated from the complexes, and the dissociation buffer (100 μL) was isolated to isolate exosomes. Moreover, 100 μL of an MgCl$_2$ solution [10 mM Tris-HCl (pH 7.4), 0.5 M MgCl$_2$] was added as a dissociation buffer to a tube containing the poly L lysine-silica magnetic beads B (0.2 mg) that contained exosomes as complexes among the tubes obtained in the above (8). Then, the tube was shaken for 5 minutes, and thus exosomes were dissociated from the complexes, and the dissociation buffer (100 μL) was isolated to isolate exosomes.

(10) For each of the two tubes (100 μL each) containing exosomes isolated in the above (9), the dissociation buffer was divided into two equal parts (first part and second part) of 50 μL and protein concentrations were measured with use of two first parts (50 μL each) divided from the respective two tubes. The measurement for the exosomes obtained with use of the K8 immobilized magnetic beads was carried out with Micro BCA Protein assay kit (available from Thermo Fisher Scientific K.K.) The measurement of a protein concentration for the exosomes obtained with use of the poly L lysine-silica magnetic beads B was carried out with Bio-Rad Protein Assay (available from Bio-Rad).

(11) With use of each of the second parts (50 μL each; corresponding to 50 μL of serum), miRNA contained in exosomes was extracted and purified in accordance with the method of the above <2>. An amount of a lysis solution used was 350 μL.

(12) For the purified miRNA, an amount of miR142-3p was quantitatively determined by qRT-PCR in accordance with the method of the above <3>, and thus an exosome amount was measured.

The protein concentration obtained in the above (10) and the exosome amount obtained in the above (12) are defined as a protein concentration after isolation and an exosome amount after isolation, respectively. Table 7 shows protein concentrations and exosome amounts after isolation with use of the K8 immobilized magnetic beads and the poly L lysine-silica magnetic beads B.

Based on Ct values in Table 7 obtained by qRT-PCR, relative concentrations of miR142-3p extracted from exosomes after isolation with use of the K8 immobilized magnetic beads and the poly L lysine-silica magnetic beads B were calculated. Here, a concentration (i.e., concentration before isolation) of miR142-3p obtained with use of miRNA directly extracted from serum supernatant was set to 1. In Table 7, the exosome amount (E)/μL is an exosome amount per 1 μL of serum, and the exosome amount (E)/protein (μg) is an exosome amount per 1 μg of protein and has been calculated based on the protein concentration (μg/μL) and the exosome amount (E) per 1 of serum. The degree of exosome purification is based on a degree of removal of contaminating protein in serum and means that, as the degree of protein removal becomes higher, the degree of exosome purification increases. Therefore, in a case where a value of the exosome amount (E)/protein (μg) is large, this means that the degree of exosome purification is high.

Here, in Table 7, a value of the exosome amount (E)/protein (μg) before isolation is defined as (x). Moreover, a value of the exosome amount (E)/protein (μg) after isolation with the K8 immobilized magnetic beads is defined as (y), and a value of the exosome amount (E)/protein (μg) after isolation with the poly L lysine-silica magnetic beads B is defined as (z).

A value (1) of x/x is defined as a degree of exosome purification before isolation, a value (4184) of y/x is defined as a degree of exosome purification after isolation with the K8 immobilized magnetic beads, and a value (4.58) of z/x is defined as a degree of exosome purification after isolation with the poly L lysine-silica magnetic beads B. Table 7 shows those degrees of exosome purification.

TABLE 7

| | Before isolation | After isolation with K8 immobilized magnetic beads | After isolation with poly L lysine-silica magnetic beads B |
|---|---|---|---|
| Relative concentration of miR142-3p ($2^{-\Delta Ct}$) | 1 | 0.20 | 0.020 |
| Protein concentration (μg/μL) | 88.364 | 0.00423 | 0.386 |
| Exosome amount/μL (E is exosome amount per 1 μL of serum) | E | 0.20E | 0.020E |
| Exosome amount (E)/protein (μg) | 0.0113 E/μg (x) | 47.281 E/μg (y) | 0.0518 E/μg (z) |
| Degree of purification | 1 (x/x) | 4184 (y/x) | 4.58 (z/x) |

With reference to the results shown in Table 7, first, amounts of exosomes (amounts of miR142-3p) are compared. It was found that, with respect to the concentration 1 before isolation, the relative concentration of miR142-3p after isolation with the K8 immobilized magnetic beads was 0.20, and the relative concentration of miR142-3p after isolation with the poly L lysine-silica magnetic beads B was 0.02.

Next, the protein concentrations are compared. With respect to the concentration 88.364 before isolation, the protein concentration after isolation with the K8 immobilized magnetic beads was 0.00423, and it was thus found that the protein concentration was extremely small as compared with the concentration before isolation. Moreover, the protein concentration after isolation with the poly L lysine-silica magnetic beads B was 0.3859 μg/μL, and it was thus found that the protein concentration was drastically decreased as compared with the concentration before isolation. From these, it was found that most of proteins in serum could be removed by the isolation method of the present invention and, in particular, in the case where the K8 immobilized magnetic beads were used, it was possible to drastically remove proteins in serum.

Next, the degrees of exosome purification are compared. Note that the degrees of exosome purification were evaluated while using the protein concentration as an indicator. It was found that approximately 4.6 times of exosomes were purified by carrying out the isolation with use of the poly L lysine-silica magnetic beads B, and approximately 4200 times of exosomes were purified by carrying out the isolation with use of the K8 immobilized magnetic beads. From these, it was found that exosomes could be purified by the isolation method of the present invention and, in particular, in a case where the K8 immobilized magnetic beads were used, exosomes could be purified with extremely high purity.

[Test Example 7] Electron Microscopy on Exosomes Isolated by Isolation Method of the Present Invention Exosomes isolated by the isolation method of the present invention were observed with an electron microscope, and thus whether or not the exosomes could be isolated in an intact state (or a substantially intact state) by the isolation method of the present invention was confirmed.

The specific experiment method is as follows:

(1) First, exosomes were collected from serum with use of the K8 immobilized magnetic beads in accordance with the method of the above <4>. Here, the K8 immobilized magnetic beads containing exosomes as complexes were cleaned with use of PBS instead of PBS (+0.01% BSA).

(2) Next, 100 µL of a KCl solution [50 mM Tris-HCl (pH 7.4), 0.5 M KCl] was added as a dissociation buffer to a tube containing the K8 immobilized magnetic beads (0.5 mg) that contained exosomes as complexes. The tube was shaken for 5 minutes, and thus exosomes were dissociated from the complexes, and the dissociation buffer (100 µL) was isolated to isolate exosomes.

(3) Next, the dissociation buffer (100 µL) containing exosomes was put in a centrifugal separator, and centrifugation was carried out at 12,000 g for 5 minutes at 4° C. Then, resultant supernatant (100 µL) was collected, and thus magnetic beads were completely removed from the dissociation buffer.

(4) 400 µL of PBS was added to the supernatant (100 µL) after centrifugation, and thus a diluted solution (0.5 mL) was prepared.

(5) The diluted solution (0.5 mL) was added to an ultrafiltration spin column (BIOMAX 50K NMWL MEMBRANE 0.5 ML VOL, available from Millipore Corporation). The ultrafiltration spin column containing the diluted solution was put in a centrifugal separator, and centrifugation was carried out at 12,000 g for 10 minutes at 4° C. By the centrifugation, the diluted solution was concentrated into approximately 50 µL, and thus an exosome concentrate was prepared.

(6) Next, exosomes were immobilized on a sample stage of electron microscope by the following procedures.

(6-1) A carbon tape was attached to the sample stage of electron microscope, and then an aluminum foil was attached onto the carbon tape.

(6-2) Onto the aluminum foil, 20 µL of a poly-L-lysine solution (molecular weight: 150,000-300,000) [available from Sigma-Aldrich] was dripped, and was then left still for 10 minutes, so that the poly-L-lysine was immobilized on the aluminum foil.

(6-3) In order to remove poly-L-lysine which had not been bound, cleaning was carried out three times with 20 µL of ultrapure water.

(6-4) Onto the sample stage of electron microscope on which poly-L-lysine had been immobilized, 20 µL of the exosome concentrate prepared in the above (5) was dripped and was then left still for 1 hour. Thus, exosomes were bound to the sample stage of electron microscope.

(6-5) Further, 20 µL of PBS containing 2.5% glutaraldehyde was dripped onto the exosomes bound to the sample stage of electron microscope and was then left still for 1 hour, and thus the exosomes were immobilized on the sample stage of electron microscope.

(7) The exosomes immobilized on the sample stage of electron microscope in the above (6) were cleaned four times with 20 µL of ultrapure water, and were then air-dried overnight at a room temperature.

(8) Platinum coating was carried out with use of AUTO FINE COATER (JFC-1600, available from JEOL Ltd.), and then exosomes were observed with a field emission scanning electron microscope (FE-SEM, SIGMA VP, available from Carl Zeiss).

Figure 9:
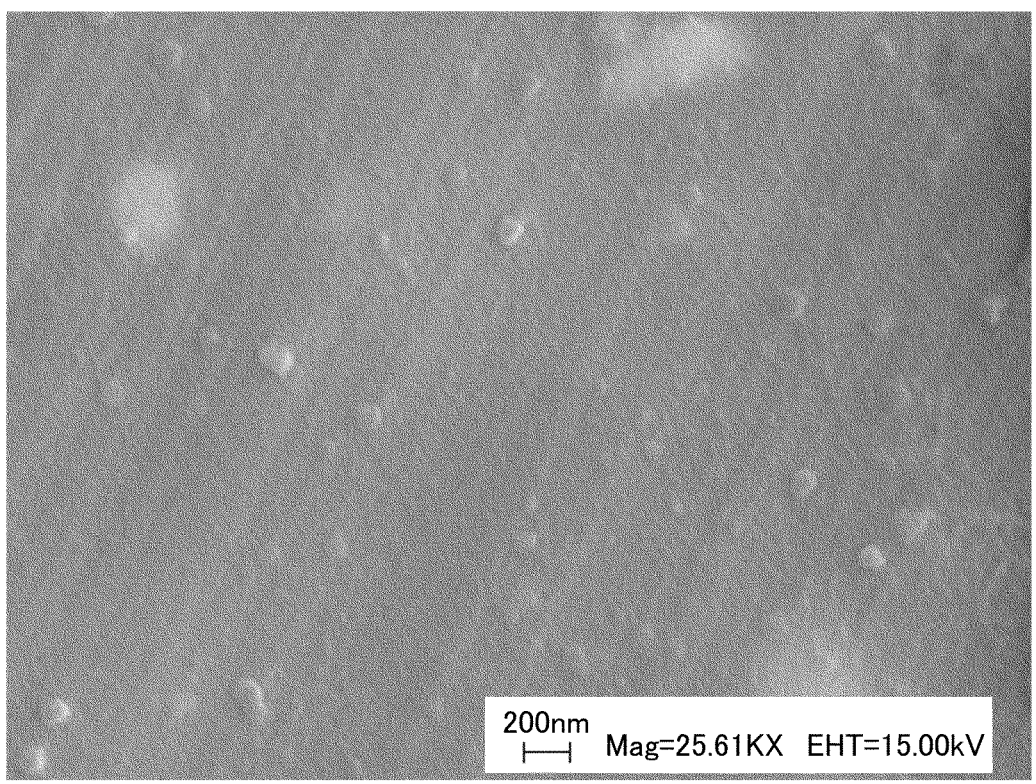
FIG. 9 is a view showing a result of electron microscopy with respect to isolated exosomes.

The result is shown in FIG. 9. FIG. 9 is a view showing a result of electron microscopy with respect to isolated exosomes.

As shown in FIG. 9, structures which seemed to be exosomes having a size of approximately 100 nm could be observed. The observed exosomes maintained the spherical form, and therefore can be considered as maintaining (or substantially maintaining) their membrane structures (specifically, lipid bilayer membranes). From this result, it was found that the isolation method of the present invention could isolate exosomes in an intact state (or a substantially intact state).

INDUSTRIAL APPLICABILITY

According to the present invention, it is possible to simply isolate an exosome in an intact state (or in a substantially intact state). Therefore, according to the present invention, it is possible to simply carry out detailed analysis on a substance contained inside an exosome. As such, the present invention is useful in various technical fields, in particular, in fields of pharmaceutical manufacture, medical treatment, and the like.

The invention claimed is:

1. A method for isolating an exosome from a sample containing the exosome, said method comprising:
a complex forming step of forming a complex by binding the exosome to a peptide supported by a carrier, the peptide containing four or more lysines which are close to each other, the carrier being capable of supporting the peptide and, in binding the exosome to the peptide, (i) the sample, the peptide, and the carrier being brought into contact with each other or (ii) the sample and the peptide supported by the carrier being brought into contact with each other; and a dissociating step of dissociating the exosome from the complex by bringing the complex which has been obtained in the complex forming step into contact with a dissociation buffer containing metal cations.

2. The method as set forth in claim 1, wherein the lysines contained in the peptide are consecutive.

3. The method as set forth in claim 1, wherein the peptide contains eight or more lysines which are close to each other.

4. The method as set forth in claim 1, wherein the carrier is magnetic beads.

5. An exosome isolation kit for carrying out the method recited in claim 1, said exosome isolation kit comprising the peptide, the carrier, and the dissociation buffer.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Artificially Synthesized Peptide Linker

<400> SEQUENCE: 1

Gly Gly Gly Ser
1

<210> SEQ ID NO 2
<211> LENGTH: 5
<212> TYPE: PRT
<213> ORGANISM: Artificial Sequence
<220> FEATURE:
<223> OTHER INFORMATION: Artificially Synthesized Peptide Linker

<400> SEQUENCE: 2

Gly Gly Gly Gly Ser

```
1               5

<210> SEQ ID NO 3
<211> LENGTH: 8
<212> TYPE: PRT
<213> ORGANISM: Artificial Sequence
<220> FEATURE:
<223> OTHER INFORMATION: Artificially Synthesized Peptide Linker

<400> SEQUENCE: 3

Gly Gly Gly Ser Gly Gly Gly Ser
1               5

<210> SEQ ID NO 4
<211> LENGTH: 12
<212> TYPE: PRT
<213> ORGANISM: Artificial Sequence
<220> FEATURE:
<223> OTHER INFORMATION: Artificially Synthesized Peptide Linker

<400> SEQUENCE: 4

Gly Gly Gly Ser Gly Gly Gly Ser Gly Gly Gly Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Artificially Synthesized Sequence

<400> SEQUENCE: 5

Gly Gly Gly Ser Gly Gly Gly Ser Gly Gly Gly Ser Lys Lys Lys Lys
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Artificially Synthesized Sequence

<400> SEQUENCE: 6

Gly Gly Gly Ser Gly Gly Gly Ser Gly Gly Gly Ser Lys Lys Lys Lys
1               5                   10                  15

Lys Lys Lys Lys
            20

<210> SEQ ID NO 7
<211> LENGTH: 24
<212> TYPE: PRT
<213> ORGANISM: Artificial Sequence
<220> FEATURE:
<223> OTHER INFORMATION: Artificially Synthesized Sequence

<400> SEQUENCE: 7

Gly Gly Gly Ser Gly Gly Gly Ser Lys Lys Lys Lys Lys Lys Lys Lys
1               5                   10                  15

Lys Lys Lys Lys Lys Lys Lys Lys
            20
```